(12) United States Patent
Svensson et al.

(10) Patent No.: US 10,940,126 B2
(45) Date of Patent: Mar. 9, 2021

(54) INHIBITION OF IL-8 IN THE TREATMENT OF PAIN AND/OR BONE LOSS

(71) Applicants: Camilla Svensson, Stockholm (SE);
Lars Klareskog, Stockholm (SE);
Vivianne Malmstrom, Stockholm (SE);
Anca Catrina, Taby (SE)

(72) Inventors: Camilla Svensson, Stockholm (SE);
Lars Klareskog, Stockholm (SE);
Vivianne Malmstrom, Stockholm (SE);
Anca Catrina, Taby (SE)

(*) Notice: Subject to any disclaimer, the term of this patent is extended or adjusted under 35 U.S.C. 154(b) by 0 days.

(21) Appl. No.: 15/393,380

(22) Filed: Dec. 29, 2016

(65) Prior Publication Data
US 2017/0181987 A1 Jun. 29, 2017

Related U.S. Application Data

(63) Continuation of application No. PCT/SE2016/050664, filed on Jun. 30, 2016.

(60) Provisional application No. 62/188,499, filed on Jul. 3, 2015, provisional application No. 62/221,119, filed on Sep. 21, 2015, provisional application No. 62/221,122, filed on Sep. 21, 2015, provisional application No. 62/221,133, filed on Sep. 21, 2015, provisional application No. 62/221,134, filed on Sep. 21, 2015, provisional application No. 62/303,452, filed on Mar. 4, 2015, provisional application No. 62/321,486, filed on Apr. 12, 2016.

(51) Int. Cl.
| | |
|---|---|
| *A61K 31/04* | (2006.01) |
| *A61K 31/18* | (2006.01) |
| *A61K 31/44* | (2006.01) |
| *A61K 31/495* | (2006.01) |
| *A61K 31/498* | (2006.01) |
| *A61K 31/4462* | (2006.01) |
| *G01N 33/68* | (2006.01) |
| *G16H 10/20* | (2018.01) |
| *A61K 31/519* | (2006.01) |
| *G06F 19/00* | (2018.01) |
| *A61K 31/185* | (2006.01) |
| *A61K 31/341* | (2006.01) |

(52) U.S. Cl.
CPC ............ *A61K 31/18* (2013.01); *A61K 31/185* (2013.01); *A61K 31/341* (2013.01); *A61K 31/4462* (2013.01); *A61K 31/495* (2013.01); *A61K 31/498* (2013.01); *A61K 31/519* (2013.01); *G01N 33/6869* (2013.01); *G06F 19/00* (2013.01); *G16H 10/20* (2018.01); G01N 2333/5421 (2013.01); G01N 2800/2842 (2013.01); G01N 2800/52 (2013.01); Y02A 90/10 (2018.01)

(58) Field of Classification Search
CPC ........ A61K 31/04; A61K 31/18; A61K 31/44; A61K 31/495; A61K 31/498
See application file for complete search history.

(56) References Cited

U.S. PATENT DOCUMENTS

| 8,859,538 B2 | 10/2014 | Beckett et al. |
| 2013/0004416 A1 | 1/2013 | Wu et al. |

FOREIGN PATENT DOCUMENTS

| EP | 1 628 665 | 3/2006 |
| WO | 2004/058797 A2 | 7/2004 |
| WO | 2004/094379 A2 | 11/2004 |

OTHER PUBLICATIONS

Miller et al. ("The pharmacokinetics and pharmacodynamics of danirixin (GSK1325756)—a selective CXCR2 antagonist—in healthy adult subjects." BMC Pharmacology and Toxicology (Jun. 20, 2015) 16:18.) (Year: 2015).*
Minden et al. (J Immunol 1966; 96:180-187). (Year: 1966).*
Barsante et al. ("Blockade of the chemokine receptor CXCR2 ameliorates adjuvant-induced arthritis in rats." Br J Pharmacol. Mar. 2008; 153(5): 992-1002) (Year: 2008).*
Hitchon et al. ("A distinct multicytokine profile is associated with anti-cyclical citrullinated peptide." J Rheumatol 2004;31;2336-2346). (Year: 2004).*
Jung et al. (J Immunol Res. 2014; 2014: 263625). (Year: 2014).*
Tammy Worth ("8 Signs and Symptoms of Rheumatoid Arthritis" Health.com (2013). https://www.health.com/health/gallery/0,,20464354,00.html). (Year: 2013).*
Novack et al. ("Inflammatory osteoclasts, a different breed of bone eaters?" Arthritis Rheumatol. Dec. 2016; 68(12): 2834-2836.) (Year: 2016).*
International Search Report for copending International Application No. PCT/SE2016/050664 dated Nov. 21, 2016.
Ahn et al., "GP.67 Changes in Expression of MRNA for Interleukin-8 and Effects of Inhibition of Microglia in the Spinal Dorsal Horn in a Rate Model of Lumbar Disc Herniation", General Posters GP67, Oct. 1, 2010.
Cunha et al., "Treatment with DF 2161, a non-competitive allosteric inhibitor of CXCR1/2, diminishes neutrophil influx and inflammatory hypernocicepti9on in mice", British Journal of Pharmacology, vol. 154, No. 2, May 1, 2008, pp. 460-470.
Sakkas et al., "Anti-citrullinated peptides as autoantigens in rheumatoid arthritis-relevance to treatment", ScienceDirect, Autoimmunity Reviews, vol. 13, No. 11, Nov. 1, 2014, pp. 1114-1120.

(Continued)

*Primary Examiner* — Jeffrey S Lundgren
*Assistant Examiner* — Chris E Simmons
(74) *Attorney, Agent, or Firm* — Clark & Elbing LLP

(57) ABSTRACT

Pain associated with a contribution of IL-8 and osteoclasts in a subject is prevented, treated and/or alleviated by the administration of an effective amount of a compound capable of inhibiting or blocking the action of interleukin 8 (IL-8). Methods and compounds for this use are disclosed, as well as a diagnostic method and kit.

9 Claims, 24 Drawing Sheets

Specification includes a Sequence Listing.

(56) References Cited

OTHER PUBLICATIONS

Ossipova et al., "Affinity purified anti-citrullinated protein/peptide antibodies target antigens expressed in the rheumatoid joint", Arthritis Research & Therapy, vol. 16, No. 4, Aug. 12, 2014, pp. 1-11.
Krishnamurthy et al., "Identification of a novel chemokine-dependent molecular mechanism underlying rheumatoid arthritis-associated autoantibody-mediated bone loss", Annals of the Rheumatic Diseases, vol. 75, No. 4, Nov. 26, 2016, pp. 721-729.
Wigerblad et al., "Autoantibodies to citrullinated proteins induce joint pain independent of inflammation via a chemokine-dependent mechanism", Annals of the Rheumatic Diseases, vol. 75, No. 4, Nov. 27, 2015, pp. 730-738.
Brink et al., "Rheumatoid factor isotypes in relation to antibodies against citrullinated peptides and carbamylated proteins before the onset of rheumatoid arthritis", Arthritis Research & Therapy, vol. 9, No. 7, Feb. 9, 2016, pp. 1-11.
Russo et al., "The CXCL8/IL-8 chemokine family and its receptors in inflammatory diseases", Expert Review of Clinical Immunology, vol. 10, No. 5, May 1, 2014, pp. 593-619.
Krishnamurthy et al."Anti-citrullinated proteins antibodies promotes osteoclastogenesis and bone destruction in rheumatoid arthritis," Ann Rheum Dis 2015 74: A43.

* cited by examiner

Cxcl1, Cxcl2, Cxcl5, Il1b, Il6, Mmp13, Mcpt4 n.d.

```
                           SEQUENCE LISTING

<160> NUMBER OF SEQ ID NOS: 8

<210> SEQ ID NO 1
<211> LENGTH: 107
<212> TYPE: PRT
<213> ORGANISM: Homo sapiens
<300> PUBLICATION INFORMATION:
<301> AUTHORS: Teeling, Jessica
      Parren, Paul
      Baadsgaard, Ole D M SC
      Hudson, Debra
      Petersen, Jorgen
<302> TITLE: Human monoclonal antibodies against interleukin 8 (il-8)
      sequence listing
<306> PAGES: 4
<310> PATENT DOCUMENT NUMBER: EP 1590364
<311> PATENT FILING DATE: 2003-12-16
<312> PUBLICATION DATE: 2011-10-05
<313> RELEVANT RESIDUES IN SEQ ID NO: SEQ ID NO 8: FROM (1) TO (107)

<400> SEQUENCE: 1

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Ile Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Pro Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Ala Gly Ser Leu
                85                  90                  95

Thr Phe Gly Pro Gly Thr Lys Val Asp Ile Lys
            100                 105

<210> SEQ ID NO 2
<211> LENGTH: 117
<212> TYPE: PRT
<213> ORGANISM: Homo sapiens
<300> PUBLICATION INFORMATION:
<301> AUTHORS: Teeling, Jessica
      Parren, Paul
      Baadsgaard, Ole D M SC
      Hudson, Debra
      Petersen, Jorgen
<302> TITLE: Human monoclonal antibodies against interleukin 8 (il-8)
      sequence listing
<306> PAGES: 5
<310> PATENT DOCUMENT NUMBER: EP 1590364
<311> PATENT FILING DATE: 2003-12-16
<312> PUBLICATION DATE: 2011-10-05
<313> RELEVANT RESIDUES IN SEQ ID NO: SEQ ID NO 12: FROM (1) TO (117)
```

```
<400> SEQUENCE: 2

Gln Val Gln Leu Val Glu Ser Gly Gly Val Val Gln Pro Gly Arg
1               5                   10                  15

Ser Leu Arg Leu Ser Cys Thr Ala Ser Gly Phe Thr Phe Ser His Tyr
            20                  25                  30

Gly Met Tyr Trp Val Arg Gln Ala Pro Gly Lys Gly Leu Glu Trp Val
        35                  40                  45

Ala Val Ile Trp Tyr Asp Gly Ser Tyr Glu Tyr Asn Glu Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Val Gly Leu Phe Asp Tyr Trp Gly Gln Gly Thr Leu
            100                 105                 110

Val Thr Val Ser Ser
        115

<210> SEQ ID NO 3
<211> LENGTH: 12
<212> TYPE: PRT
<213> ORGANISM: Homo sapiens
<300> PUBLICATION INFORMATION:
<301> AUTHORS: Teeling, Jessica
         Parren, Paul
         Baadsgaard, Ole D M SC
         Hudson, Debra
         Petersen, Jorgen
<302> TITLE: Human monoclonal antibodies against interleukin 8 (il-8)
         sequence listing
<306> PAGES: 6
<310> PATENT DOCUMENT NUMBER: EP 1590364
<311> PATENT FILING DATE: 2003-12-16
<312> PUBLICATION DATE: 2011-10-05
<313> RELEVANT RESIDUES IN SEQ ID NO: SEQ ID NO 16: FROM (1) TO (12)

<400> SEQUENCE: 3

Arg Ala Ser Gln Ser Ile Ser Ser Ser Tyr Leu Ala
1               5                   10

<210> SEQ ID NO 4
<211> LENGTH: 7
<212> TYPE: PRT
<213> ORGANISM: Homo sapiens
<300> PUBLICATION INFORMATION:
<301> AUTHORS: Teeling, Jessica
         Parren, Paul
         Baadsgaard, Ole D M SC
         Hudson, Debra
         Petersen, Jorgen
<302> TITLE: Human monoclonal antibodies against interleukin 8 (il-8)
         sequence listing
<306> PAGES: 6
<310> PATENT DOCUMENT NUMBER: EP 1590364
<311> PATENT FILING DATE: 2003-12-16
<312> PUBLICATION DATE: 2011-10-05
<313> RELEVANT RESIDUES IN SEQ ID NO: SEQ ID NO 17: FROM (1) TO (7)

<400> SEQUENCE: 4

Gly Pro Ser Ser Arg Ala Thr
1               5

<210> SEQ ID NO 5
<211> LENGTH: 8
<212> TYPE: PRT
<213> ORGANISM: Homo sapiens
```

```
<300> PUBLICATION INFORMATION:
<301> AUTHORS: Teeling, Jessica
          Parren, Paul
          Baadsgaard, Ole D M SC
          Hudson, Debra
          Petersen, Jorgen
<302> TITLE: Human monoclonal antibodies against interleukin 8 (il-8)
          sequence listing
<306> PAGES: 6
<310> PATENT DOCUMENT NUMBER: EP 1590364
<311> PATENT FILING DATE: 2003-12-16
<312> PUBLICATION DATE: 2011-10-05
<313> RELEVANT RESIDUES IN SEQ ID NO: SEQ ID NO 18: FROM (1) TO (8)

<400> SEQUENCE: 5

Gln Gln Tyr Ala Gly Ser Leu Thr
1               5

<210> SEQ ID NO 6
<211> LENGTH: 5
<212> TYPE: PRT
<213> ORGANISM: Homo sapiens
<300> PUBLICATION INFORMATION:
<301> AUTHORS: Teeling, Jessica
          Parren, Paul
          Baadsgaard, Ole D M SC
          Hudson, Debra
          Petersen, Jorgen
<302> TITLE: Human monoclonal antibodies against interleukin 8 (il-8)
          sequence listing
<306> PAGES: 7
<310> PATENT DOCUMENT NUMBER: EP 1590364
<311> PATENT FILING DATE: 2003-12-16
<312> PUBLICATION DATE: 2011-10-05
<313> RELEVANT RESIDUES IN SEQ ID NO: SEQ ID NO 22: FROM (1) TO (5)

<400> SEQUENCE: 6

His Tyr Gly Met Tyr
1               5

<210> SEQ ID NO 7
<211> LENGTH: 17
<212> TYPE: PRT
<213> ORGANISM: Homo sapiens
<300> PUBLICATION INFORMATION:
<301> AUTHORS: Teeling, Jessica
          Parren, Paul
          Baadsgaard, Ole D M SC
          Hudson, Debra
          Petersen, Jorgen
<302> TITLE: Human monoclonal antibodies against interleukin 8 (il-8)
          sequence listing
<306> PAGES: 7
<310> PATENT DOCUMENT NUMBER: EP 1590364
<311> PATENT FILING DATE: 2003-12-16
<312> PUBLICATION DATE: 2011-10-05
<313> RELEVANT RESIDUES IN SEQ ID NO: SEQ ID NO 23: FROM (1) TO (17)

<400> SEQUENCE: 7

Val Ile Trp Tyr Asp Gly Ser Tyr Glu Tyr Asn Glu Asp Ser Val Lys
1               5                   10                  15

Gly

<210> SEQ ID NO 8
<211> LENGTH: 8
<212> TYPE: PRT
<213> ORGANISM: Homo sapiens
```

```
-continued

<300> PUBLICATION INFORMATION:
<301> AUTHORS: Teeling, Jessica
        Parren, Paul
        Baadsgaard, Ole D M SC
        Hudson, Debra
        Petersen, Jorgen
<302> TITLE: Human monoclonal antibodies against interleukin 8 (il-8)
        sequence listing
<306> PAGES: 7
<310> PATENT DOCUMENT NUMBER: EP 1590364
<311> PATENT FILING DATE: 2003-12-16
<312> PUBLICATION DATE: 2011-10-05
<313> RELEVANT RESIDUES IN SEQ ID NO: SEQ ID NO 24: FROM (1) TO (8)

<400> SEQUENCE: 8

Asp Arg Val Gly Leu Phe Asp Tyr
1               5
```

INHIBITION OF IL-8 IN THE TREATMENT OF PAIN AND/OR BONE LOSS

This application is a continuation of International Application No. PCT/SE2016/050664 filed Jun. 30, 2016 and published in the English language, which claims priority to US Provisional Application Nos. U.S. 62/188,499 filed Jul. 3, 2015, U.S. 62/221,119 filed Sep. 21, 2015, U.S. 62/221,122 filed Sep. 21, 2015, U.S. 62/221,133 filed Sep. 21, 2015, U.S. 62/221,134 filed Sep. 21, 2015, and U.S. 62/303,452 filed Mar. 4, 2016. This application claims priority to US Provisional Application No. U.S. 62/321,486 filed Apr. 12, 2016.

TECHNICAL FIELD

The present description relates generally to methods and compounds for the treatment, including the alleviation and/or prevention of pain and where applicable also treatment of bone loss or bone destruction in individuals where IL-8 and/or osteoclasts contribute to pain and/or bone loss or bone destruction, including individuals at risk to develop a disease, individuals in the early stages of a disease before clinical symptoms are identified, i.e. before onset of a disease, and individuals diagnosed as having a disease involving pain and/or bone loss or bone destruction.

The description relates in particular to the inhibition or blockade of the action of interleukin 8 (IL-8) as a step in the alleviation and/or prevention of pain, including methods to this end, as well as compounds for use in such methods. Steps of a diagnostic method and components of a diagnostic kit are also disclosed.

BACKGROUND

Pain is associated with many different conditions and diseases. Regardless of etiology, pain can be incapacitating, severely impairing the quality of life of an individual. There are different approaches to treat pain, the two main avenues being the administration of opioids, acting through their effect on the central nervous system; and anti-inflammatory drugs, relieving pain by reducing inflammation.

The most widely used group of anti-inflammatory drugs are called non-steroidal anti-inflammatory drugs, commonly abbreviated NSAIDs. NSAIDs alleviate pain by counteracting the cyclooxygenase (COX) enzyme. On its own, the COX enzyme synthesizes prostaglandins, creating inflammation. In whole, the NSAIDs prevent the prostaglandins from being synthesized, reducing or eliminating the pain.

The use of opioids is associated with many side effects, such as tolerance development and abuse. Also anti-inflammatory drugs are known to cause side-effects. It has for example been shown that long-term use of NSAIDs can cause gastric erosions, which can develop into stomach ulcers and in extreme cases cause severe hemorrhage, resulting in death. The risk of death as a result of gastrointestinal bleeding caused by the use of NSAIDs increases with age, and should be taken into account when prescribing NSAIDs to elderly (over 75 years). Other dangers of NSAIDs include possible exacerbation of asthma and causing kidney damage. Apart from aspirin, prescription and over-the-counter NSAIDs also increase the risk of myocardial infarction and stroke.

Bone loss or bone destruction (hereafter only referred to as "bone loss"), i.e. the de-mineralization of bone, manifested e.g. as a reduction of bone density, is also associated with many different conditions and diseases. Regardless of etiology, bone loss can have very severe consequences, including but not limited to bone deformation and fractures. Bone loss is often, but not always, associated with pain, irrespective of whether the bone loss has resulted in symptoms such as deformation and/or fractures.

Autoimmune diseases are examples of diseases, which are frequently associated with pain and in many cases also associated with bone loss. The prevalence of autoimmune diseases is rising. Although each individual disease may not be overly common, the collective number is remarkable. It is estimated that at least 5% of the population in Europe and USA is affected today. Pain is a common symptom which is often associated with serious disabilities and decreased quality of life. In many autoimmune diseases, bone loss is also an accompanying effect of the disease.

Arthritis is among the most common autoimmune diseases, and joint pain (arthralgia) is a common symptom. Interestingly, joint pain is common also in individuals at risk for arthritis, but who do not yet have inflammation in the joints (synovitis) as well as in patients with arthritis, where inflammation has been successfully treated ("remaining pain").

There is a significant medical need to treat pain and in particular joint pain both in individuals who are at risk for arthritis but still without concurrent joint inflammation, patients with active inflammation and arthritis, and in patents with arthritis who have been successfully treated for their inflammation, but who still suffer from joint pain. The situations with pain but without active synovitis, both before and after active joint inflammation, differ in very important ways from pain in individuals with joint inflammation. During inflammation the major mechanisms for pain are associated with the inflamed states, and with pro-inflammatory molecules such as TNF, IL-1 and IL-6 that are released during inflammation. Other mechanisms are in play in the situation without active synovitis.

During inflammation, pain is often relieved with anti-inflammatory treatments that involve blockade of the above mentioned molecules and other cytokines. Such therapies however have little or no effect on "remaining pain" and there is at present no evidence that such therapies would be effective in individuals at risk for rheumatoid arthritis who suffer from arthralgia and other types of pain, but have no joint inflammation.

Rheumatoid arthritis (RA) is a chronic inflammatory joint disease. Antibodies against-citrullinated protein/peptide antigens (ACPAs) occur in a majority of patients and are highly specific for RA. ACPAs consist of a collection of antibodies with different specificities toward citrullinated antigens. It is generally known that ACPAs may occur many years before the onset of joint inflammation, and their presence has been associated with bone destruction (Rantapää-Dahlqvist et al., 2003; Harre et al., JCI 2012; Catrina et al., Immunol Rev, 2016).

Citrullination is a post-translational modification where arginine (Arg) is converted to citrulline (Cit) by an enzymatic reaction catalyzed by peptidylarginine deiminases (PAD). In vitro activation of PAD enzymes is known to require high levels of calcium. In humans, the PAD family is composed of five, calcium dependent isozymes (PADs 1-4 and 6) which share roughly 50% sequence similarity. PADs are found in a myriad of cell and tissue types, including the epidermis and uterus (PAD1), skeletal muscle, brain, inflammatory cells, several cancer cell lines, and secretory glands (PAD2), hair follicles and keratinocytes (PAD3), granulocytes and several types of cancer (PAD4), and oocytes and embryos (PAD6).

Citrullination was originally described as a physiological process in the terminal differentiation of the epidermis and during brain development, but is also shown to be a central event in the context of inflammation (Makrygiannakis et al., 2006).

As indicated above, another important medical problem is bone loss, including the related indications osteopenia and osteoporosis, as well as bone destruction in conjunction with joint inflammation, including joint inflammation in rheumatoid arthritis and other inflammatory arthritic conditions. Bone loss is characterized by a decrease in bone mass and density that sometimes result in an increased predisposition to fractures. Bone loss can occur in many different conditions, for example but not limited to hormonal imbalances such as in postmenopausal women, nutritional deficiencies such as insufficient supply of calcium or vitamin D, thyroid conditions, as a side effect of different medications, for example corticosteroids and anti-seizure medications, and as a result of different diseases, such as cystic fibrosis, and cancer, e.g. multiple myeloma. Joint inflammation (arthritis) is a particularly common and serious cause behind bone loss and bone destruction. Many factors may interact, and for example smoking, alcohol abuse and a sedentary life style can further worsen the condition.

Bone density is defined as the amount of bone tissue in a certain volume of bone. It can be quantified in different ways, for example measured using ultrasound, dual X-ray absorptiometry (DXA), dual energy X-ray absorptiometry (DEXA), or a special X-ray called quantitative computed tomography (QCT).

Osteopenia is a condition in which the bone density is lower than normal. It is considered by many doctors to be a precursor to osteoporosis. However, not every person diagnosed with osteopenia will develop osteoporosis.

U.S. Pat. No. 8,859,538 discloses methods and compounds for prophylaxis, treatment or inhibition of a cannabinoid receptor-associated disease, disorder or condition in a mammalian subject, mentioning inter alia IL-8 and claims methods for anti-inflammatory treatment of conditions associated with elevated levels of IL-8, e.g. RA. The patent describes the effects of blockade of IL-8 only in the context of inflammation, it does not specify the treatment of pain, it does not mention any role of ACPAs, nor does it mention any role of osteoclasts.

US 20130004416A1 discloses binding proteins for the treatment of inflammatory diseases, including RA, and including acute and chronic pain, but does not disclose the inhibition or blockade of IL-8.

EP1628665 discusses the inhibition of IL-8 in the treatment of RA but without specifying the treatment of pain. It describes the effects of inhibition of IL-8 only in the context of inflammation, it does not mention any role of ACPAs, and it does not mention any role of osteoclasts.

In the article by Endo et al., Clinical and experimental Immunology, Vol. 96, Issue 1, 1 Apr. 1994, a long term infusion of human recombinant IL-8 into the knee joints of New Zealand white rabbits was shown to result in arthritis characterized by apparent erythema, the accumulation of leucocytes, infiltration of mononuclear cells in synovial tissue, and marked hypervascularization in the synovial lining layer. Endo et al. hypothesize that IL-8 may be a factor which can contribute to the inflammatory process of chronic arthritis by mediating leucocyte recruitment and hypervascularization in inflamed joints. No experimental studies on pain or on involvement of osteoclasts are described.

S. Riegsecker and S. Ahmed, FASEB, 2013; 27:643.18, 1 Apr. 2013. The authors showed that epigallocatechin-3-gallate (EGCG), a polyphenol found in green tea, inhibited the induction of IL-8 production in RA synovial fibroblasts, suggesting that EGCG could decrease inflammation and inhibit joint damage in RA. The article describes the effects of inhibition of IL-8 production only in the context of inflammation, it does not mention any role of ACPAs, and it does not mention any role of osteoclasts.

Tanaka et al., Modern Rheumatology, Vol. 22, issue 1, 1 Feb. 2012: In this article, the authors hypothesize that suppression of inter alia IL-8 could be a route to suppress the pathogenesis of TNF alpha-induced RA. The article describes the effects of inhibiting IL-8 only in the context of inflammation, it does not specify the treatment of pain in RA, it does not mention any role of ACPAs, and it does not mention any role of osteoclasts.

Cao, D.-L., Zhang, Z.-J., Xie, R.-G., Jiang, B.-C., Ji, R.-R., & Gao, Y.-J. (2014). Chemokine CXCL1 enhances inflammatory pain and increases NMDA receptor activity and COX-2 expression in spinal cord neurons via activation of CXCR2. *Experimental Neurology*. Intraplantar CFA. Intrathecal (spinal) injection of CXCL1 neutralizing antibody, CXCR2-inhibitor, and CXCL1. These data demonstrate intrathecal mechanisms for pain induction involving IL-8. There is however no data in this article showing any role of IL-8 in pain induced outside the thecal space, and the article specifically does not mention neither joint pain nor any role of antibodies in general or ACPAs in particular in the induction of pain.

Zhang, Z.-J., Cao, D.-L., Zhang, X., Ji, R.-R., & Gao, Y.-J. (2013). Chemokine contribution to neuropathic pain: respective induction of CXCL1 and CXCR2 in spinal cord astrocytes and neurons. *Pain*, 154(10), 2185-2197. The article relates to nerve injury induced pain. Intrathecal injection of CXCL1 neutralizing antibody, CXCR2-inhibitor, and CXCL1. CXCL1 shRNA in spinal cord. Again, no data exist in this article that mention any role of IL-8 in pain induced outside the thecal space, and does specifically mention neither joint pain nor any role of antibodies in general or ACPAs in particular in the induction of pain.

Qin, X., Wan, Y., & Wang, X. (2005). CCL2 and CXCL1 trigger calcitonin gene-related peptide release by exciting primary nociceptive neurons. *Journal of Neuroscience Research*, 82(1), 51-62. Intraplantar injection of CXCL1 induces production of a pain-related molecular mechanism in nociceptive neurons. No data and no suggestions exist in this article that link IL-8 to joint pain or to presence and any role of ACPAs.

Guerrero, A. T. G., Cunha, T. M., Verri, W. A., Gazzinelli, R. T., Teixeira, M. M., Cunha, F. Q., & Ferreira, S. H. (2012). Toll-like receptor 2/MyD88 signaling mediates zymosan-induced joint hypernociception in mice: participation of TNF-α, IL-1β and CXCL1/KC. *European Journal of Pharmacology*, 674(1), 51-57. Zymosan inflammation. Intra-articular injection of CXCL1. Systemic CXCR2-inhibition. This pain is induced only in conjunction with joint inflammation and the article does not mention any role of ACPAs nor any role of osteoclasts.

Kim, S.-J., Park, S.-M., Cho, Y.-W., Jung, Y.-J., Lee, D.-G., Jang, S.-H., et al. (2011). Changes in expression of mRNA for interleukin-8 and effects of interleukin-8 receptor inhibitor in the spinal dorsal horn in a rat model of lumbar disc herniation. *Spine*, 36(25), 2139-2146. Lumbar disc herniation model of pain. This pain can be blocked with an inhibitor of the IL-8 receptor. Also this study addresses central processes, and does not address pain in joints and does no mention any role of ACPAs or osteoclasts.

Cui, G.-B., An, J.-Z., Zhang, N., Zhao, M.-G., Liu, S.-B., & Yi, J. (2012). Elevated interleukin-8 enhances prefrontal synaptic transmission in mice with persistent inflammatory pain. *Molecular Pain*, 8(1), 11. Also this article focuses on central effects and processes and does not address any role of ACPAs or other antibodies.

WO 2004/058797 discloses isolated human monoclonal antibodies which bind to human IL-8, as well as bi-specific and multi-specific molecules and other therapeutic compositions containing such antibodies, alone or in combination with additional therapeutic agents. Also provided are methods for treating a variety of IL-8 mediated diseases using antibodies and compositions disclosed in WO 2004/058797.

Therefore, the antibodies of WO 2004/058797 provide an improved means for treating and preventing disorders mediated by IL-8 activity attributable in part to their unique specificity (e. g. epitope specificity and lack of cross-reactivity with related chemokines), affinity, structure, functional activity and the fact that they are fully human, making them significantly less immunogenic and more therapeutically effective and useful when administered to human patients than other IL-8 antibodies previously generated (e. g., murine and humanized antibodies).

While mentioning rheumatoid arthritis, WO 2004/058797 however only mentions pain associated with RA indirectly and only in one passage: A "therapeutically effective dosage" for rheumatoid arthritis preferably will result in an ACR20 Preliminary Definition of Improvement in the patients, more preferred in an ACR50 Preliminary Definition of Improvement and even more preferred in an ACR70 Preliminary Definition of Improvement. ACR20 Preliminary Definition of Improvement is defined as: 20% improvement in: Tender Joint Count (TJC) and Swollen Joint Count (SJC) and 20% improvement in 3 of following 5 assessments: Patient Pain Assessment (VAS), Patient Global assessment (VAS), Physician Global Assessment (VAS), Patient Self-Assessed Disability (HAQ), and Acute Phase Reactant (CRP or ESR).

Notably, WO 2004/058797 does not address the problem of bone loss in rheumatoid arthritis, but only generally mentions that the antibodies disclosed can be used for treating diseases wherein interfering with interactions between IL-8 and osteoclasts is beneficial, such as osteoporosis, and osteolytic metastases. Further, WO 2004/058797 is apparently silent on the role of autoantibodies in pain and/or bone loss, and entirely silent on the issue of remaining pain.

Cuhna et al., Treatment with DF 2162, a non-competitive allosteric inhibitor of CXCR1/2 diminishes neutrophil influx and inflammatory hypernociception in mice, British Journal of Pharmacology, 154:2, May 2008, 460-470. In this study the role of CXCR1/2-mediated neutrophil influx was examined, mainly as an element in the cascade of events leading to inflammation-induced pain. The authors show that DF2162, a CXCR1/2 antagonist inhibits neutrophil recruitment induced by injection of the chemokine CXCL1 or carrageenan to the paw and draw the conclusion that the prevention of neutrophil infiltration is the mechanisms by which CXCL1 and carrageenan-induced pain-like behavior is blocked. They state that the DF2162 compound does not directly affect nociceptor sensitization.

SUMMARY

One aim of the present inventors was to better understand the mechanisms behind pain, and to develop new approaches to the treatment, including the prevention and/or alleviation of pain.

As a first aspect, the inventors make available a method of preventing and/or alleviating pain in a subject wherein said pain is associated with the contribution of IL-8 and osteoclasts in said subject, wherein an effective amount of a compound is administered to said subject, said compound being capable of inhibiting or blocking the action of IL-8.

According to an embodiment of said first aspect, said compound I compound is a CXCR1/2 antagonist. Preferably, said compound is an allosteric CXCR1/2 inhibitor, which blocks CXCR1 and/or CXCR2 function by blocking receptor signalling instead of chemokine binding.

More preferably said compound is chosen from the compounds exemplified in Table 1 below:

TABLE 1

Examples of CXCR1/2 antagonists

| Tradename, synonym | IUPAC-name |
|---|---|
| Reparixin, repertaxin, DF 1681Y | (2R)-2-[4-(2-methylpropyl)phenyl]-N-methylsulfonylpropanamide |
| DF 2162 | 4-[(1R)-2-amino-1-methyl-2-oxoethyl]phenyl trifluoromethane sulfonate |
| AZD8309 | 5-[[(2,3-Difluorophenyl)methyl]thio]-7-[[(1R)-2-hydroxy-1-methylethyl]amino]-thiazolo[4,5-d]pyrimidin-2(3H)-one |
| AZD5069 | N-[2-[[(2,3-difluoropheny)methyl]thio]-6-{[(1R,2S)-2,3-dihydroxy-1-methylpropyl]oxy}-4-pyrimidinyl]-1-azetidinesulfonamide |
| PD0220245 | N-(3-[2,20]bithiophenyl-5-yl-6,7-dichloroquinoxalin-2-yl)-N,N-diethyl-butane-1,4-diamine•dihydrochloride. |
| SB-332235 | 1-(4-chloro-2-hydroxy-3-sulfamoylphenyl)-3-(2,3-dichlorophenyl)urea |
| SCH-527123, Navarixin | 2-hydroxy-N,N-dimethyl-3-[[2-[[(1R)-1-(5-methylfuran-2-yl)propyl]amino]-3,4-dioxocyclobuten-1-yl]amino]benzamide |
| SB-656933, Elubrixin | 1-(2-chloro-3-fluorophenyl)-3-(4-chloro-2-hydroxy-3-piperazin-1-ylsulfonylphenyl)urea |
| SB-225002 | N-(2-chloro-3-fluorophenyl)-N'-[4-chloro-2-hydroxy-3-(piperazin-1-ylsulfonyl) phenyl]-urea |
| GSK1325756, Danirixin | 1-[4-chloro-2-hydroxy-3-[(3S)-piperidin-3-yl]sulfonylphenyl]-3-(3-fluoro-2-methylphenyl)urea |

According to a specific embodiment of said first aspect said compound is reparixin (repertaxin, (2R)-2-[4-(2-methylpropyl)phenyl]-N-methylsulfonylpropanam ide).

According to another specific embodiment of said first aspect said compound is danirixin (1-[4-chloro-2-hydroxy-3-[(3S)-piperidin-3-yl]sulfonylphenyl]-3-(3-fluoro-2-methylphenyl)urea.

According to another embodiment of said first aspect, said compound is an anti-IL-8 antibody or an antibody capable of reacting with CXCR1/2.

Preferably this is an antibody capable of binding to IL-8 and to inhibit IL-8 function (and IL-8 mediated effects) by blocking IL-8 binding to its receptor for the treatment of pain. For example, this antibody is preferably an antibody capable of inhibiting pro-inflammatory and angiogenic effects induced by IL-8, such as IL-8 induced chemotactic activity for leukocytes and IL-8 induced calcium flux. The antibody can also inhibit IL-8 induced increased expression of CDIIb (Mac-1) and decreased expression of L-selectin (CD62L).

More preferably said antibody is an isolated human monoclonal antibody which binds to human IL-8, comprising the six CDR sequences VLCDR1 of SEQ ID NO: 3 (also herein identified as SEQ ID NO: 16 disclosed in European Application No. 1590364 A4 (EP1590364A4), which publication is incorporated by reference herein in its entirety), VLCDR2 of SEQ ID NO: 4 (also herein identified as SEQ ID NO: 17 disclosed in EP1590364A4), VLCDR3 of SEQ ID NO: 5 (also herein identified as SEQ ID NO: 18 disclosed in EP1590364A4), VHCDR1 of SEQ ID NO: 6 (also herein identified as SEQ ID NO: 22 disclosed in EP1590364A4), VHCDR2 of SEQ ID NO: 7 (also herein identified as SEQ ID NO: 23 disclosed in EP1590364A4), and VH CDR3 of SEQ ID NO: 8 (also herein identified as SEQ ID NO: 24 disclosed in EP1590364A4).

Said antibody is preferably an antibody as defined above, which further comprises a variable heavy chain amino acid sequence as set forth in SEQ ID NO: 2 (also herein identified as SEQ ID NO: 12 disclosed in EP 1590364A4) and/or a variable light chain amino acid sequence as set forth in SEQ ID NO: 1 (also herein identified as SEQ ID NO: 8 disclosed in EP1590364A4).

More preferably the antibody is selected from an IgG1, an IgG2, an IgG3, an IgG4, an IgM, an IgA1, an IgA2, a secretory IgA, an IgD and an IgE antibody. Still more preferably the antibody is an IgG 1,κ or IgG 1,λ isotype or, alternatively, said antibody is an IgG4,κ or IgG4,λ isotype. More preferably, said antibody comprises an IgG I or IgG3 heavy chain.

Preferably said antibody has one or more of the following characteristics:
(i) inhibits IL-8 binding to its receptors (CXCR1 and CXCR2);
(ii) inhibits IL-8 induced pro-inflammatory effects;
(iii) inhibits IL-8 induced chemotactic activity for neutrophils;
(iv) inhibits IL-8 induced calcium flux;
(v) inhibits IL-8 induced changes in expression levels of adhesion molecules or neutrophils;
(vi) inhibits IL-8 induced increased expression of CD11b (Mac-1) and inhibits IL-8 induced decreased expression of L-selectin on neutrophils;
(vii) does not cross-react with related chemokines selected from human GRO-α, human GRO-β, human IP-10 and human NAP-2;
(viii) significantly inhibits chemotaxis induced by biological fluids which contain multiple chemotactic factors including IL-8.

Examples of suitable antibodies include, but are not limited to ABX-IL8, a fully humanized monoclonal anti-CXCL8 antibody produced by Abgenix, and HuMax®-IL8, a high affinity fully human antibody developed by GenMab A/S, and directed towards IL-8.

Most preferably said antibody is HuMax®-IL8.

According to a second aspect, the inventors make available a method of preventing and/or alleviating pain in a subject wherein said pain is associated with the contribution of IL-8 and osteoclasts in said subject, wherein the presence of IL-8 and activation of osteoclasts is associated with the presence of autoantibodies in said subject, wherein an effective amount of a compound capable of inhibiting or blocking the action of IL-8 is administered to said subject.

Said autoantibodies preferably comprise or consist predominantly of anti-citrullinated protein antibodies (ACPA) and/or antibodies cross-reacting with targets of ACPAs. More preferably, said autoantibodies are anti-citrullinated protein antibodies (ACPA). Thus, according to an embodiment of said second aspect, said autoantibodies are anti-citrullinated protein antibodies (ACPA).

A normal value of ACPA is about 20 EU/ml or less, whereas a level in the range of about 20 to about 39 EU/ml is considered weakly positive, or weakly elevated, about 40 to about 59 EU/ml is considered moderately positive or moderately elevated, whereas above 60 EU/ml is considered strongly positive, or strongly elevated. There are of course individual and genetic variations, but a treating physician will be able to determine if a given patient exhibits elevated levels of ACPA. Importantly, there are indications that the effects of ACPAs and of other antibodies may be further enhanced if also rheumatoid factors (RF) are present.

The term rheumatoid factor and factors (abbreviated RF) collectively refers to antibodies directed against the Fc fragment of immunoglobulin G (IgG). They are heterogeneous and usually composed of immunoglobulin M (IgM). RFs are used as a marker in individuals with suspected rheumatoid arthritis (RA) or other autoimmune conditions, and there are commercially available assays for the detection of RFs, mainly IgM.

The normal reference range for RF is considered to be less than 15 IU/mL. Consequently, and applicable to all embodiments listed in the disclosure, including the examples and claims, the presence of autoantibodies in combination with RFs is a potential marker both in the identification of patients that are likely to benefit from the treatments disclosed herein, and a marker for observing the effects of a drug, and/or the progression/remission of a disease.

According to an embodiment of said second aspect, said autoantibodies are detectable in a sample taken from said patient, but wherein the patient does not manifest clinical signs of an autoimmune disease.

According to a specific embodiment of said second aspect, said autoimmune disease is chosen from rheumatoid arthritis, osteoarthritis, and arthralgia.

According to an embodiment, freely combinable with the above embodiments of said second aspect, said compound is a CXCR1/2 antagonist.

Preferably said compound is an allosteric CXCR1/2 inhibitor, which blocks CXCR1 and/or CXCR2 function by blocking receptor signalling instead of chemokine binding.

According to another embodiment of said second aspect, said compound is chosen from the compounds exemplified in Table 1 above, incorporated herein by reference.

According to a specific embodiment of said second aspect said compound is reparixin (repertaxin, (2R)-2-[4-(2-methylpropyl)phenyl]-N-methylsulfonylpropanam ide).

According to another specific embodiment of said second aspect said compound is danirixin, 1-[4-chloro-2-hydroxy-3-[(3S)-piperidin-3-yl]sulfonylphenyl]-3-(3-fluoro-2-methylphenyl)urea.

According to another embodiment of said second aspect, said compound is an anti-IL-8 antibody or an antibody capable of reacting with CXCR1/2.

Preferably this is an antibody capable of binding to IL-8 and to inhibit IL-8 function (and IL-8 mediated effects) by blocking IL-8 binding to its receptor for the treatment of pain. For example, this antibody is preferably an antibody capable of inhibiting pro-inflammatory and angiogenic effects induced by IL-8, such as IL-8 induced chemotactic activity for leukocytes and IL-8 induced calcium flux. The antibody can also inhibit IL-8 induced increased expression of CDIIb (Mac-1) and decreased expression of L-selectin (CD62L).

More preferably said antibody is an isolated human monoclonal antibody which binds to human IL-8, comprising the six CDR sequences VLCDR1 of SEQ ID NO: 3, VLCDR2 of SEQ ID NO: 4, VLCDR3 of SEQ ID NO: 5, VHCDR1 of SEQ ID NO: 6, VHCDR2 of SEQ ID NO: 7 and VH CDR3 of SEQ ID NO: 8.

Said antibody is preferably an antibody as defined above, which further comprises a variable heavy chain amino acid sequence as set forth in SEQ ID NO: 2 and/or a variable light chain amino acid sequence as set forth in SEQ ID NO: 1.

More preferably the antibody is selected from an IgG1, an IgG2, an IgG3, an IgG4, an IgM, an IgA1, an IgA2, a secretory IgA, an IgD and an IgE antibody. Still more preferably the antibody is an IgG 1,κ or IgG 1,λ isotype or, alternatively, said antibody is an IgG4,κ or IgG4,λ isotype. More preferably, said antibody comprises an IgG I or IgG3 heavy chain.

Preferably said antibody has one or more of the following characteristics:
(i) inhibits IL-8 binding to its receptors (CXCR1 and CXCR2);
(ii) inhibits IL-8 induced pro-inflammatory effects;
(iii) inhibits IL-8 induced chemotactic activity for neutrophils;
(iv) inhibits IL-8 induced calcium flux;
(v) inhibits IL-8 induced changes in expression levels of adhesion molecules or neutrophils;
(vi) inhibits IL-8 induced increased expression of CD11b (Mac-1) and inhibits IL-8 induced decreased expression of L-selectin on neutrophils;
(vii) does not cross-react with related chemokines selected from human GRO-α, human GRO-β, human IP-10 and human NAP-2;
(viii) significantly inhibits chemotaxis induced by biological fluids which contain multiple chemotactic factors including IL-8.

Examples of suitable antibodies include, but are not limited to ABX-IL8, a fully humanized monoclonal anti-CXCL8 antibody produced by Abgenix, and HuMax®-IL8, a high affinity fully human antibody developed by GenMab A/S, and directed towards IL-8.

Most preferably said antibody is HuMax®-IL8.

One aspect of the invention is thus the use of HuMax®-IL8 for preventing and/or alleviating pain in a subject wherein said pain is associated with the contribution of IL-8 and/or osteoclasts in said subject, wherein the action of IL-8 and/or the contribution of osteoclast activity in said subject is/are associated with the presence of autoantibodies in said subject, in particular an elevated level of said autoimmune antibodies.

Another aspect is the use of an IL-8 antagonist for the alleviation and/or prevention of pain associated with the contribution of IL-8 and osteoclasts in a subject.

According to an embodiment of said aspect, the presence of IL-8 and an activation of osteoclasts are associated with the presence of autoantibodies in the subject. Preferably said autoantibodies are anti-citrullinated protein antibodies (ACPA).

According to an embodiment of said aspect, said IL-8 antagonist is a CXR1/2 antagonist. Preferably said IL-8 antagonist is chosen from the compounds exemplified in Table 1 above, incorporated herein by reference.

According to a specific embodiment, said compound is reparixin (repertaxin, (2R)-2-[4-(2-methylpropyl)phenyl]-N-methylsulfonylpropanamide). A specific aspect is thus the use of repertaxin for the alleviation and/or prevention of pain, in particular pain associated with the contribution of IL-8 and osteoclasts in a subject.

According to another specific embodiment, said compound is danirixin, 1-[4-chloro-2-hydroxy-3-[(3S)-piperidin-3-yl]sulfonylphenyl]-3-(3-fluoro-2-methylphenyl)urea.

A specific aspect is thus the use of danirixin for the alleviation and/or prevention of pain, in particular pain associated with the contribution of IL-8 and osteoclasts in a subject.

According to an embodiment, said autoantibodies are detectable in a sample taken from said patient, but wherein said patient does not manifest clinical signs of an autoimmune disease.

Another aspect relates to a diagnostic method and/or a diagnostic kit for identifying individuals that would benefit from the above mentioned treatment, the alleviation or prevention of pain, wherein said method and/or kit comprises one or more of the following steps or components:
an assay for determining the level of IL-8 in serum;
an assay for determining the level of IL-8 in synovial fluid;
an assay for determining increased production of Il-8 from osteoclasts;
an assay for determining the presence and identity of autoantibodies, including presence of antibodies to citrullinated antigens and/or rheumatoid factors (RF); and
a questionnaire for quantitatively and optionally qualitatively assessing pain, and in particular joint pain (arthralgia).

According to a particular embodiment, said kit further comprises means for qualitatively or quantitatively assessing bone density and/or the degree of bone loss.

Another aspect relates to a method for identifying individuals that would benefit from treatment according to any one of above aspects and embodiments, wherein said method comprises one or more of the following steps:
determining the level of IL-8 in serum,
determining the level of IL-8 in synovial fluid,
determining the presence of an increased production of IL-8 from osteoclasts
determining the presence and identity of autoantibodies, including presence of antibodies to citrullinated antigens and/or the presence of rheumatoid factors (RF), and
quantitatively and optionally qualitatively assessing pain.

Preferably said method further comprises a step of qualitatively or quantitatively assessing bone density and/or the degree of bone loss.

Further aspects and embodiments thereof will become apparent to a skilled person upon study of the description, examples, drawings and attached claims.

BRIEF DESCRIPTION OF DRAWINGS

The invention is now described, by way of example, with reference to the accompanying drawings, in which.

Figures 2A, 2B:
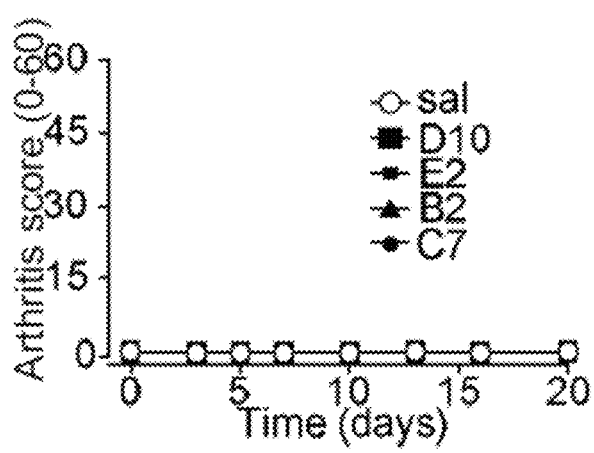
Figure 2C:
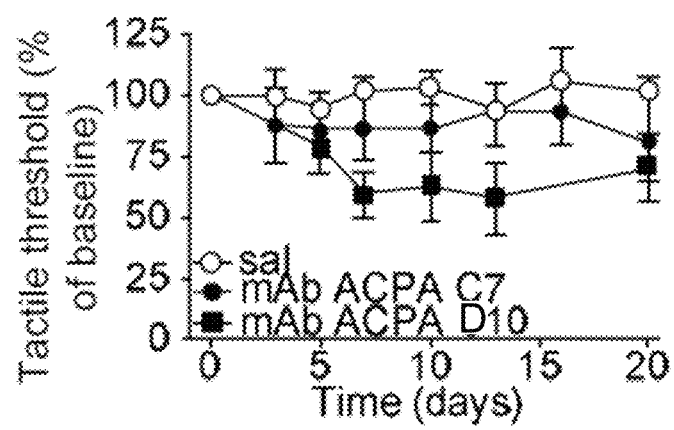
Figure 2D:
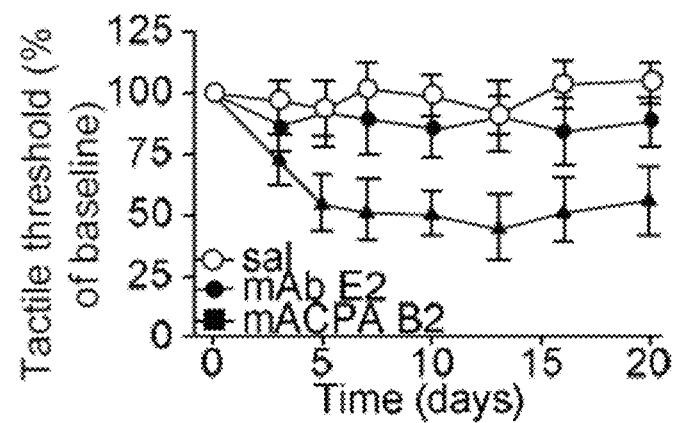

FIGS. 2A-2D depict the mechanical sensitivity following injection of murinized monoclonal ACPAs in mice. Specificities of the monoclonal antibodies derived from B cells of human RA-patients measured with ELISA, using CEP-1, fib36-52, vim60-75, and CCP peptides. Control antibody E2 binds human tetanus (FIG. 2A). Visual inflammation score (0-60) for all monoclonal antibodies (FIG. 2B). Two mg of D10 (n=12) (FIG. 2C), C7 (n=7) (FIG. 2C), B2 (n=7) (FIG. 2D), control antibody E2 (n=7) (FIG. 2D) or saline (sal, n=18) (FIGS. 2C and 2D) were injected and mechanical sensitivity was measured over 20 days. Data are presented as mean±S.E.M. *=P<0.05; =P<0.01; *=P<0.001 compared to saline.

Figure 3A:
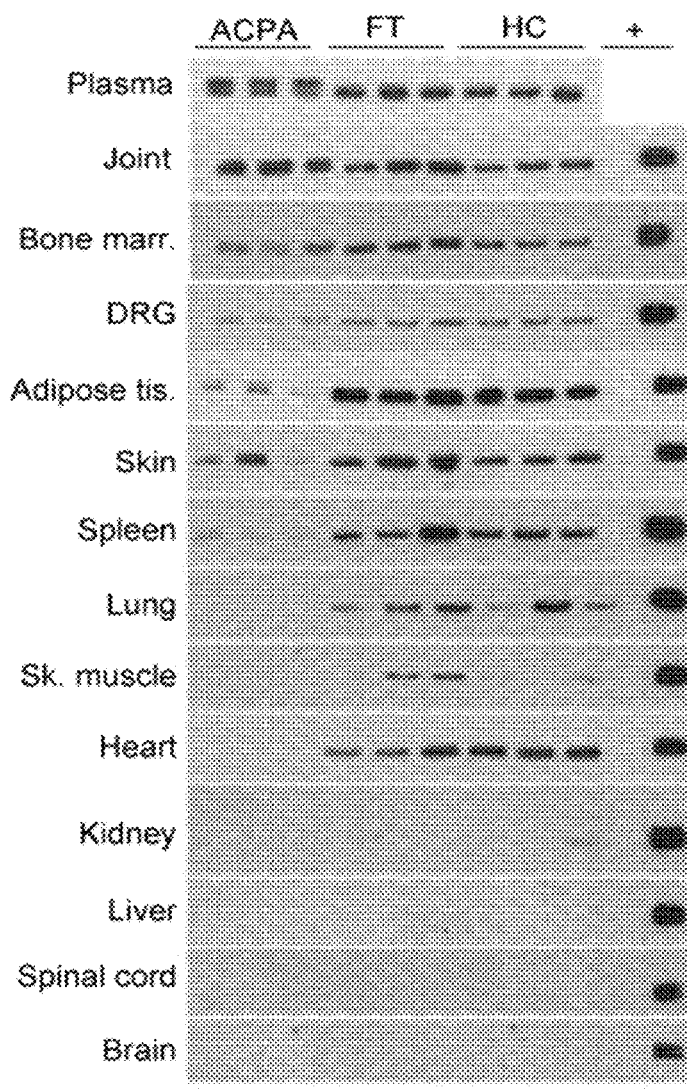
Figure 3B:
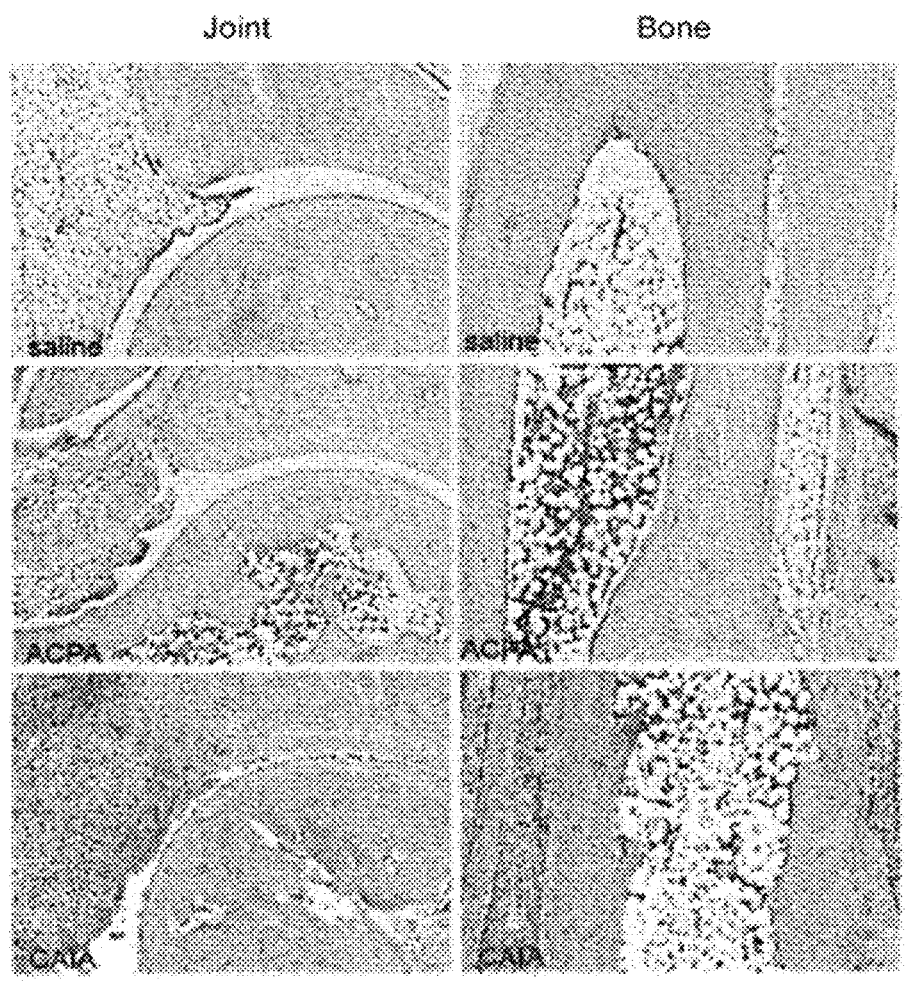
Figure 3C:
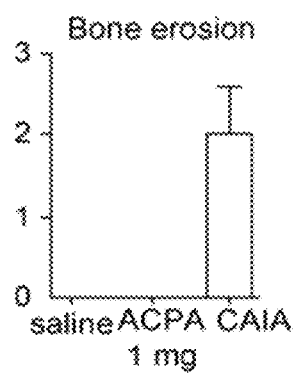
Figure 3D:
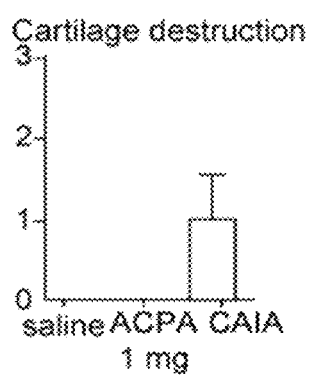
Figure 3E:
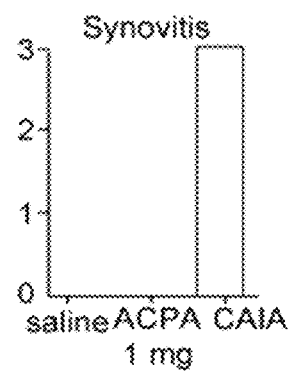
Figure 3F:
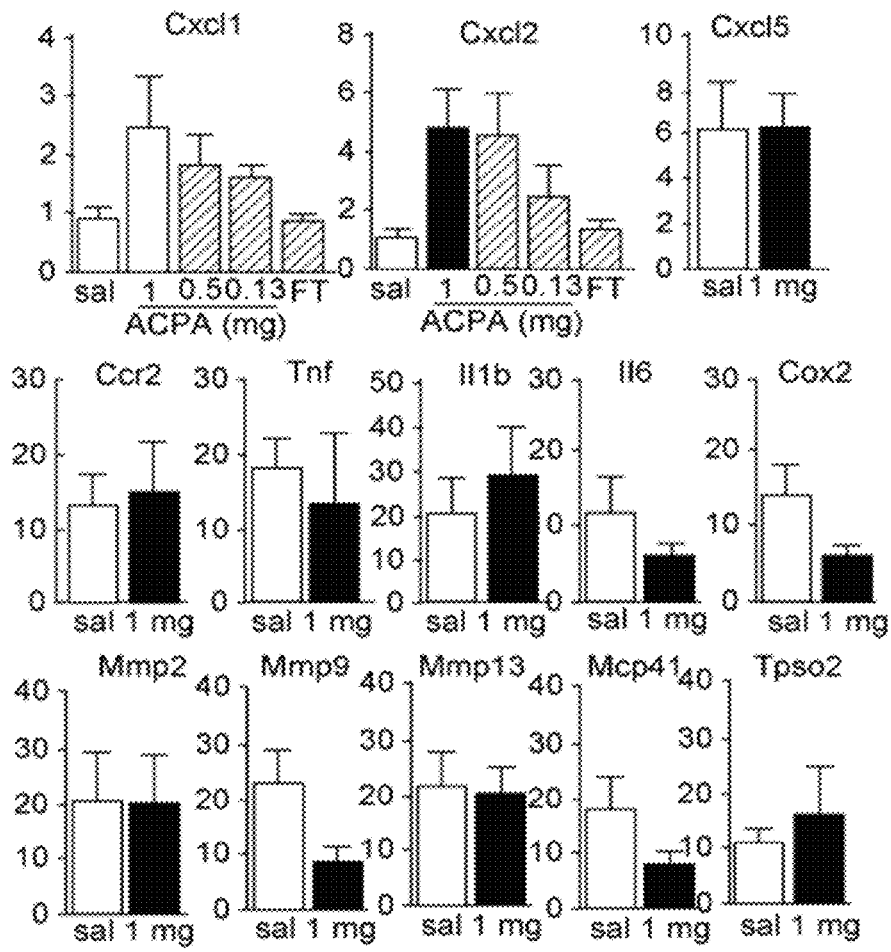

FIGS. 3A-3G illustrate the location of antibodies, histology, and gene expression in mice after injection of human ACPAs. Mice were perfused with saline (sal) to remove blood and presence of human IgG in different tissues 7 days after i.v. injection of 1 mg of ACPA3, FT3, or IgG from healthy control (HC) was assessed by western blot. Plasma was used as positive control (FIG. 3A). Representative ankle joint and tibial bone sections stained with hematoxylin and eosin (H&E, Histolab) 7 days after injection of human ACPA3 (n=3), saline (n=4), or 15 days after induction of collagen antibody-induced arthritis (CAIA, positive control) (n=3) (FIG. 3B), were scored for bone erosion (FIG. 3C), loss of cartilage (FIG. 3D), and synovitis (FIG. 3E). Ankle joint extracts were analyzed by qPCR for changes in mRNA levels 7 days after injection of human ACPA2-3 (n=6) or saline (n=6) and data expressed as relative expression unit (REU) (FIG. 3F). Fluorescence image of paws (FIG. 3G), presented as a heat map after i.v. injection with MMPsense680, which becomes fluorescent in the presence of active MMPs in mice injected with saline, human ACPA3, or anti-collagen antibodies as positive control (n=3/group). Data are presented as mean±S.E.M *=P<0.05; =P<0.01; *=P<0.001 compared to saline.

Figure 4A:
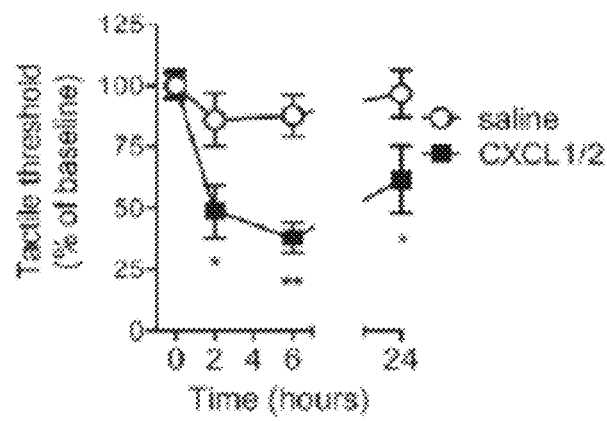
Figure 4B:
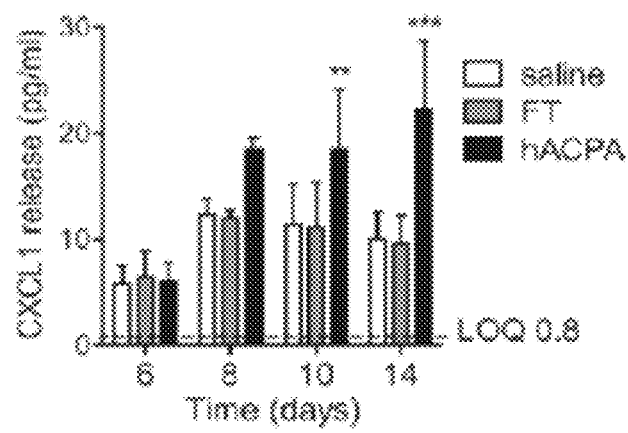
Figure 4C:
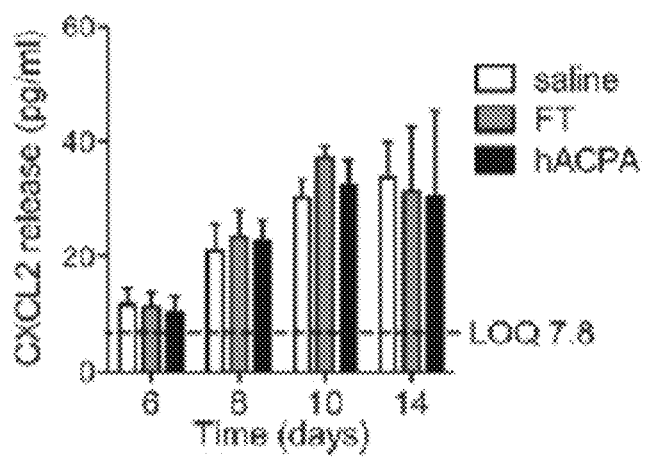
Figure 4D:
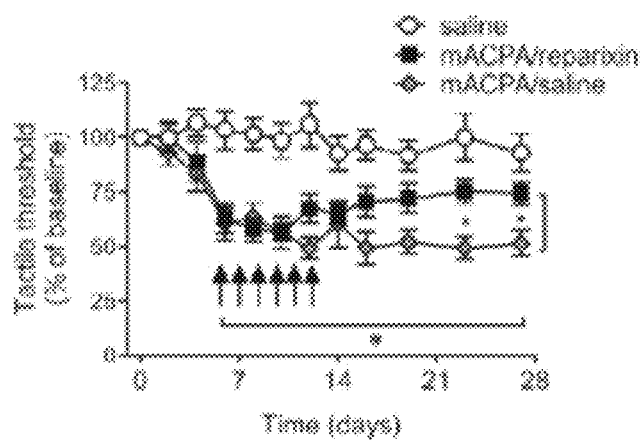
Figure 4E:
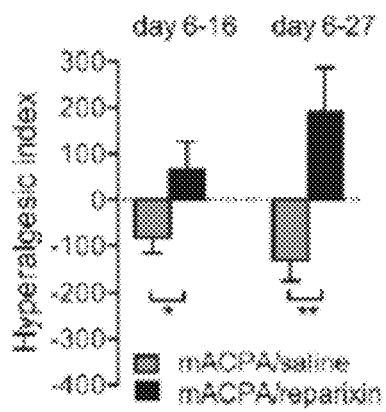
Figure 4F:
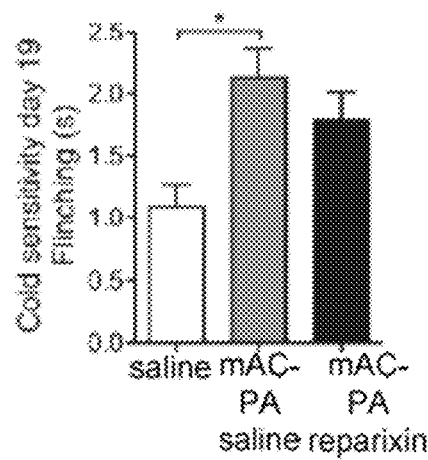
Figure 4G:
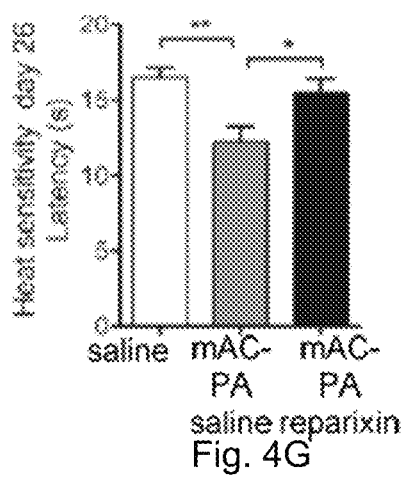

FIGS. 4A-4D depict the mechanical sensitivity after intraarticular injection of CXCL1/CXCL2 and effect of CXCR1/2 antagonist on ACPA-induced pain-like behavior. Mechanical hypersensitivity after injection of CXCL1 and CXCL2 (15 ng each, n=10) or saline (n=13) into the ankle joint (FIG. 4A). CXCL1 and CXCL2 levels in the supernatant of cultured mouse osteoclasts after stimulation with human ACPA (1 μg/ml), FT (1 μg/ml), or saline (n=6 mice/group). Three different cohorts of littermates were used (FIGS. 4B and 4C). Mechanical sensitivity after i.v. injection of mouse monoclonal ACPA D10 and B2 (1 mg each, n=18) or saline (n=9) and treatment with reparixin (30 mg/kg/day, s.c., n=9) or saline (n=9) for six days, starting day 6 (FIG. 4D). Hyperalgesic index comparing the area under the curve (AUC) for reparixin or saline treated mice from day 6 (FIG. 4E). Cold (FIG. 4F) and heat (FIG. 4G) sensitivity were tested day 19 and 26, respectively. Results are from two separate experiments. Statistical significance (2 way ANOVA) between mACPA/saline and saline is marked # and difference between mACPA/saline and mACPA/reparixin is marked *. Data are presented as mean±S.E.M. * or #=P<0.05; =P<0.01; *=P<0.001 compared to saline.

Figure 5A:
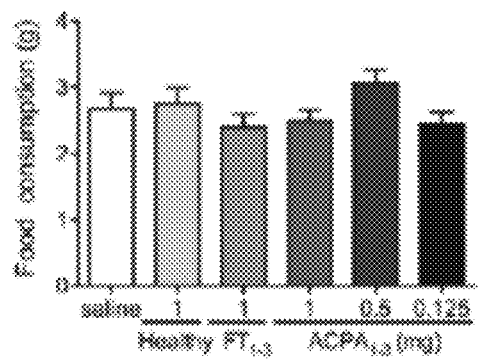
Figure 5B:
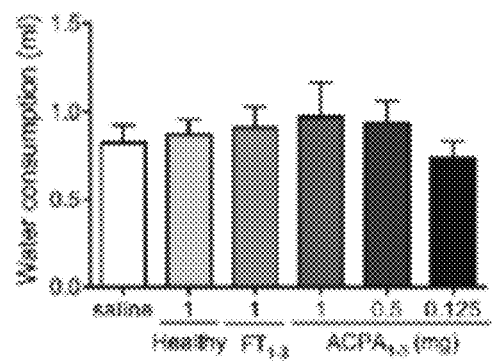
Figure 5C:
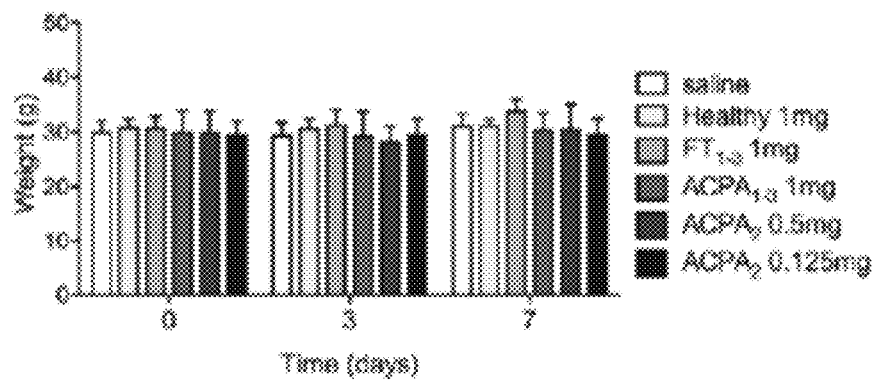
Figure 5D:
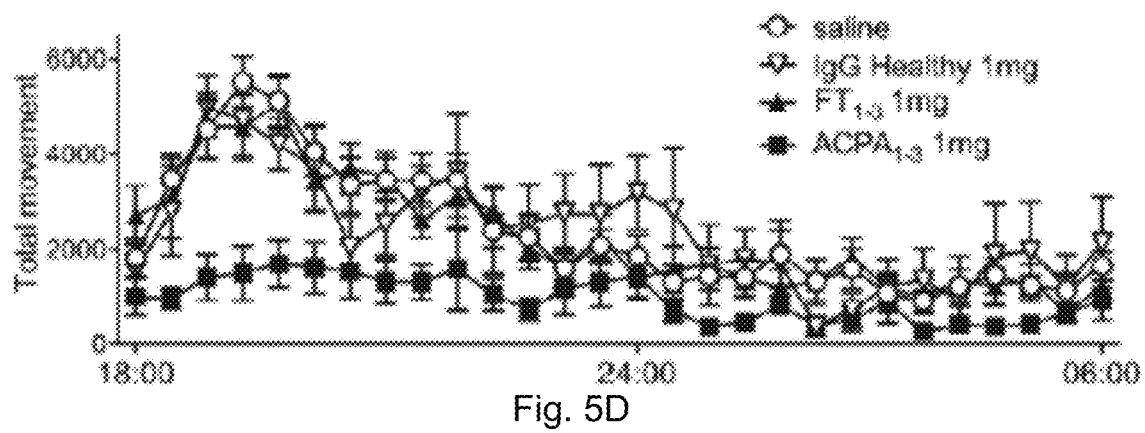

FIGS. 5A-5D illustrate locomotor activity and physiological parameters in mice injected with human antibodies. Summary of mice injected with saline (n=18), IgG from healthy donors (n=6), human ACPA1-3 (n=10), and FT1-3 (n=18), monitored for food (FIG. 5A) and water (FIG. 5B) consumption, and movement (FIG. 5D) during the third night after injection. Body weight of the mice at baseline, 3, and 7 days after injection (FIG. 5C).

Figure 6A:
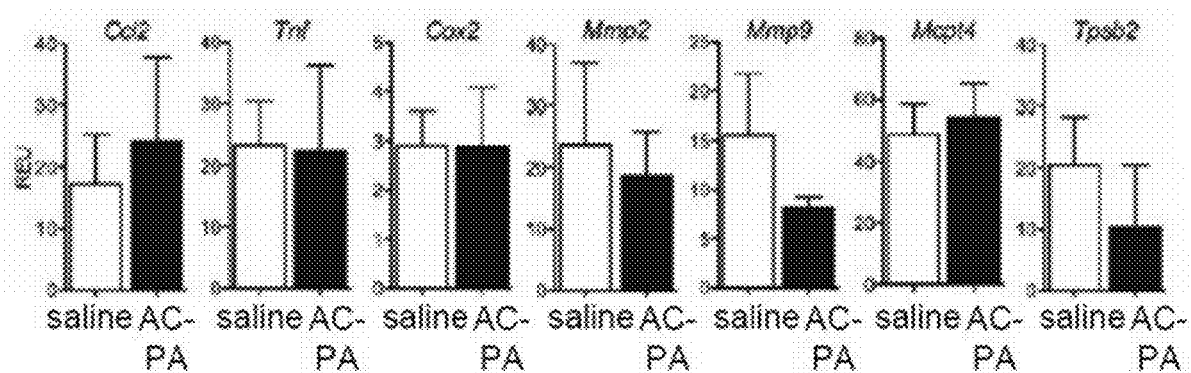
Figure 6B:
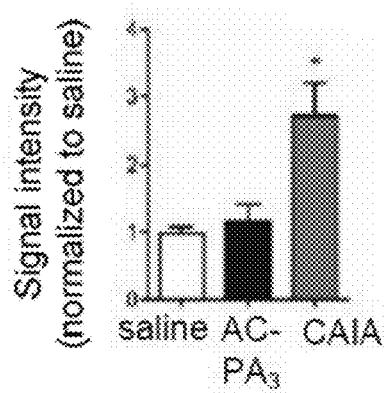

FIGS. 6A and 6B show the expression of genes in the skin from plantar hind paw in mice and fluorescence after injection of human antibodies. Extracts from the plantar skin of the hind paw were analyzed by qPCR for changes in mRNA levels for different factors 7 days after injection of human ACPA3 or saline and the data expressed as relative expression unit (REU). N.d. means not detectable (FIG. 6A). Quantification of fluorescence in the paws after injection of MMPsense, in mice treated injected with ACPA3, saline, or CAIA as positive control (n=3/group). Normalized to saline (FIG. 6B).

Figure 7A:
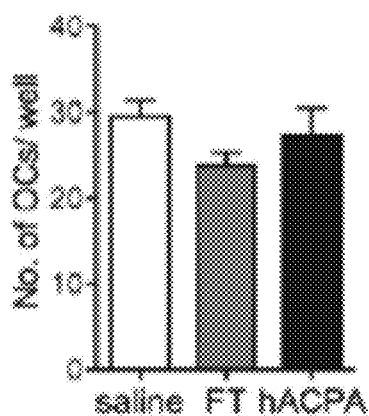
Figure 7B:
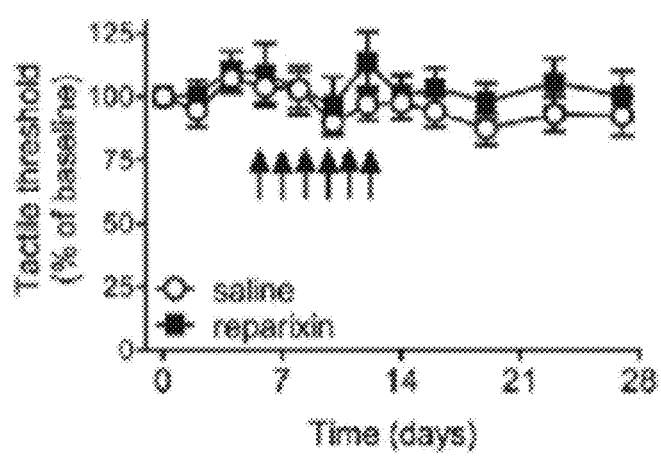

FIGS. 7A and 7B show the number of osteoclasts per well after 14 days of culture and stimulation from day 6 with hACPA (1 μg/ml), corresponding FT (1 μg/ml), or saline (FIG. 7A). Mechanical sensitivity in naïve mice subjected to treatment with reparixin (n=5) or saline (n=5) for six days (FIG. 7B).

Figure 8:
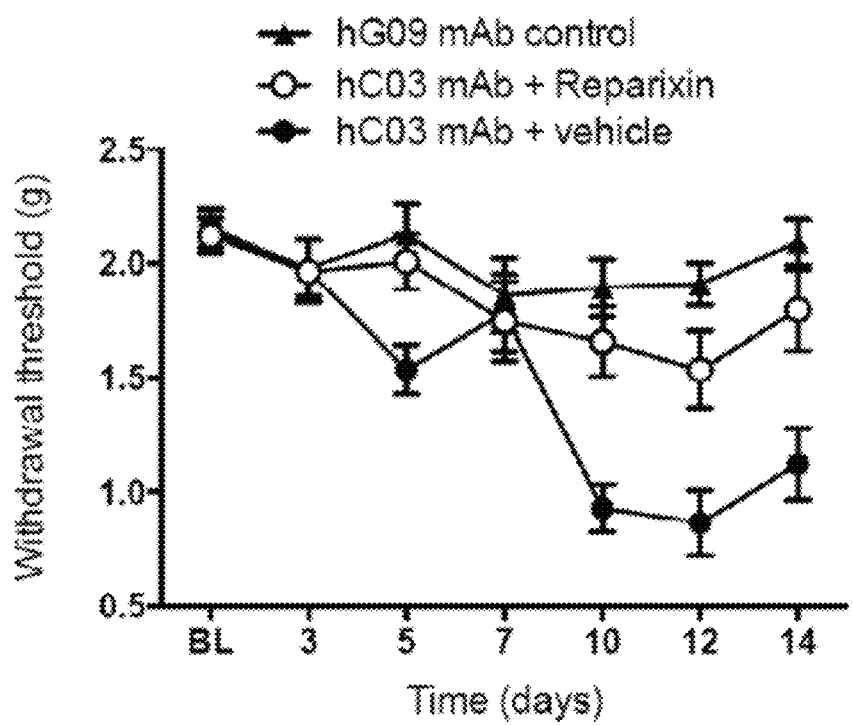
Figure 9A:
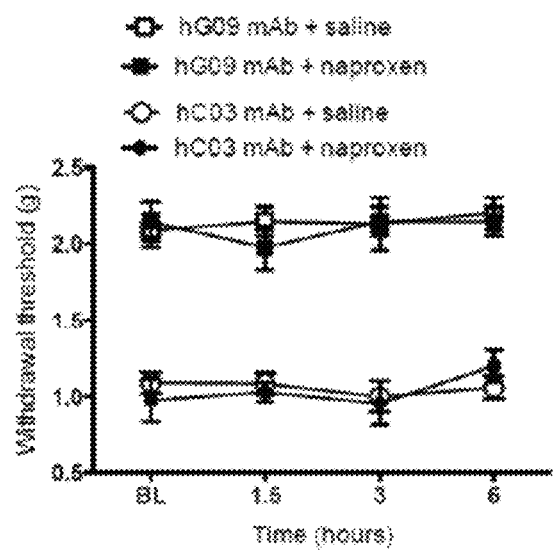
Figure 9B:
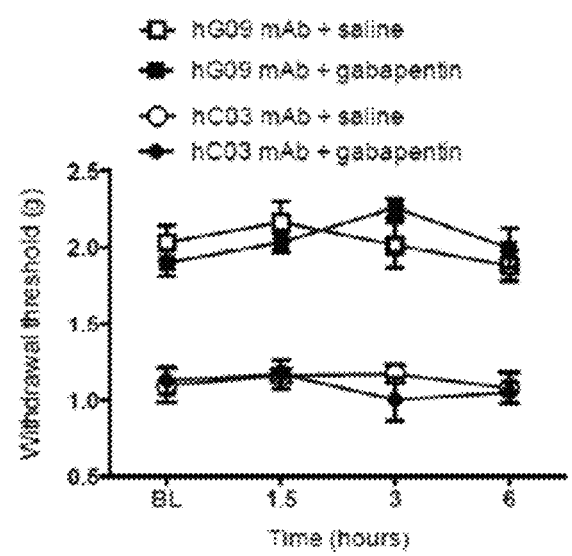
Figure 9C:
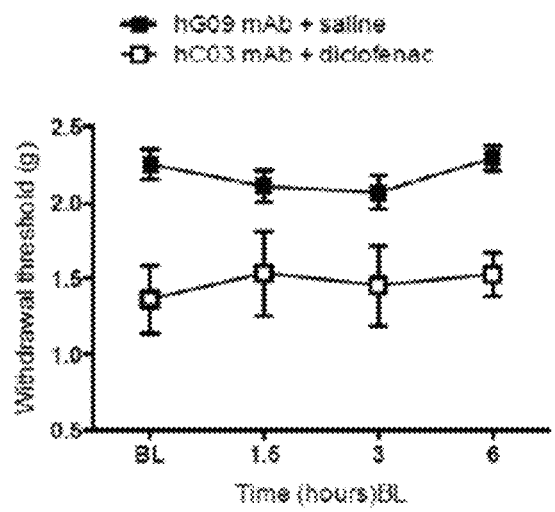
Figure 9D:
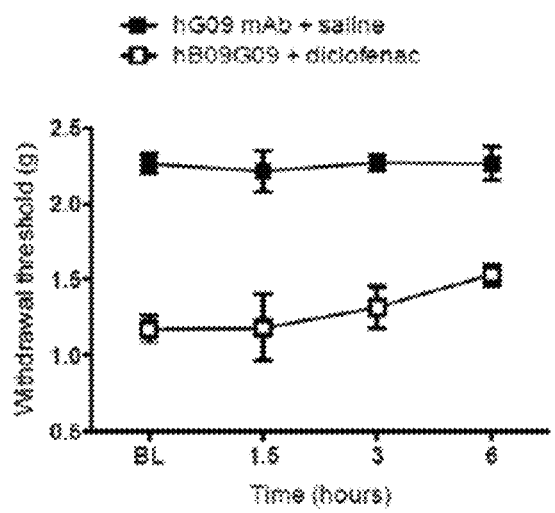

FIG. 8 shows the attenuating effects of reparixin on pain, measured as withdrawal threshold in an animal model, where pain was induced through the injection of human monoclonal ACPA antibodies hG09 and hC03.

FIGS. 9A-9D show the apparent lack of effect of the painkillers naproxen (FIG. 9A), gabapentin (FIG. 9B) and diclofenac (FIGS. 9C and 9D) on pain, measured as withdrawal threshold in an animal model, where the pain was induced through the injection of human monoclonal ACPA antibodies hG09 and hC03.

Figure 10:
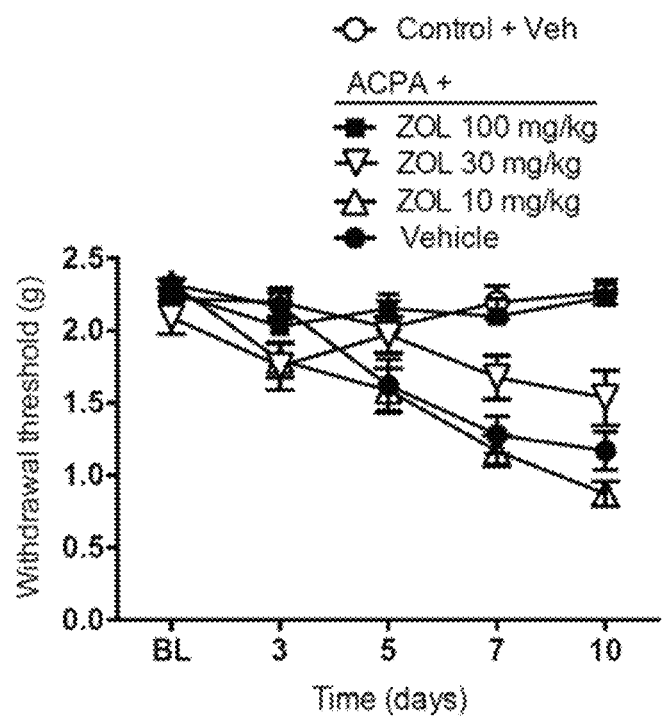

FIG. 10 is a graph showing the dose-dependent effect of zoledronate on ACPA induced pain (hD10/hB02, mAb 1 mg each), measured as withdrawal threshold.

Figure 1A:
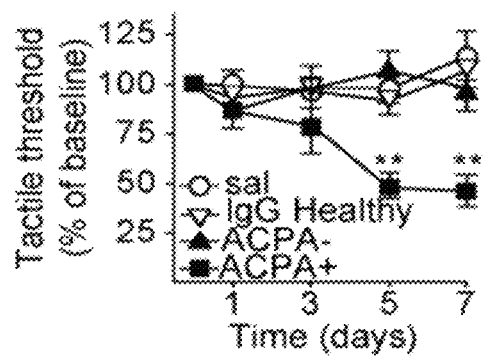
FIGS. 1A-1N are graphs depicting the mechanical and thermal sensitivity and locomotor activity in mice following injection of human antibodies. Mechanical sensitivity in mice injected i.v. with saline (sal), IgG from healthy donors, IgG from ACPA– RA patients, or IgG from ACPA+ RA patients (4 mg, n=9/group) (FIG. 1A) and purified human (h) ACPA IgG (batch 1, 1 mg, n=4), non-ACPA IgG from the same patients (FT, 1 mg, n=6) and IgG from healthy donors (1 mg, n=6) (FIG. 1B). ACPA and FT from batch 1 were injected into a different strain of mice (n=7/group) and mechanical sensitivity assessed over time (FIG. 1C), cold sensitivity day 7 and day 28 (FIGS. 1E and 1F, respectively) and heat sensitivity day 25 (FIG. 1G). Total movement (FIG. 1H), ambulatory (directional) movement (FIG. 1I), and rearing (FIG. 1J) were monitored 12 h the third night (same mice as in FIG. 1C). Arthritis scores (0-60) (FIG. 1D). Mechanical sensitivity day 5 and 7 (FIG. 1K) and total movement (FIG. 1L), ambulatory movement (FIG. 1M), and rearing (FIG. 1N) during third night after injection with 1 mg ACPA batch 1-3, (n=3 each) or 0.5 mg (n=7), 0.125 mg (n=6) ACPA batch 2 or corresponding FT (n=6/group), or saline. Data are presented as mean±S.E.M. *=P<0.05; =P<0.01; *=P<0.001 compared to saline.
Figure 1B:
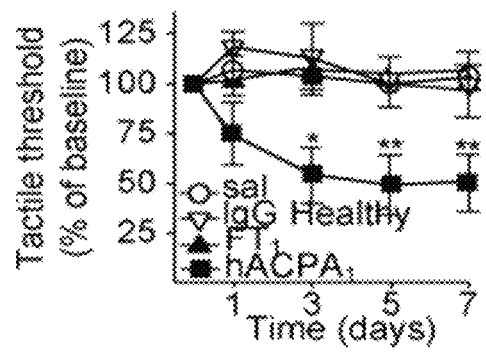
Figure 1C:
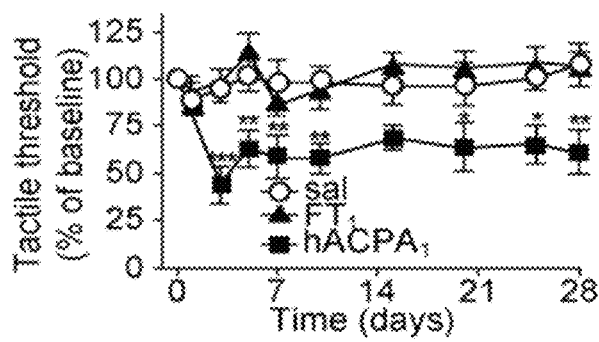
Figure 1D:
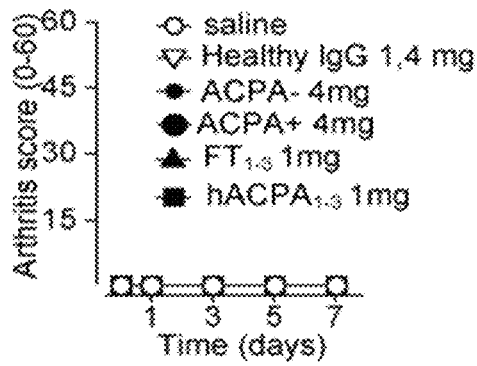
Figure 1E:
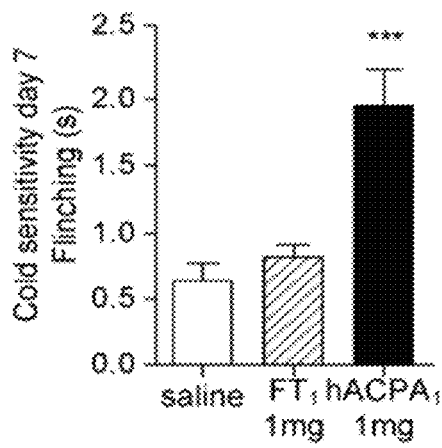
Figure 1F:
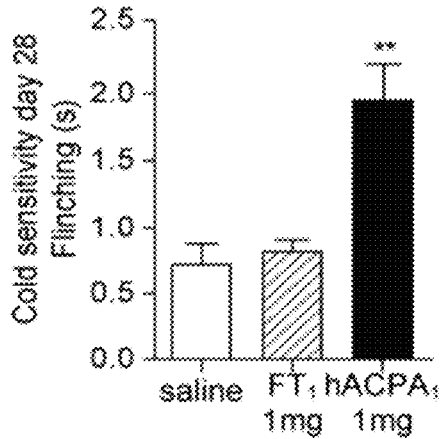
Figure 1G:
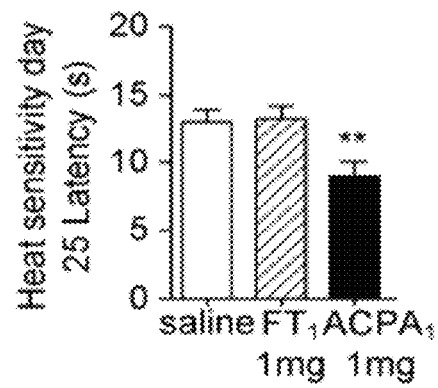
Figure 1H:
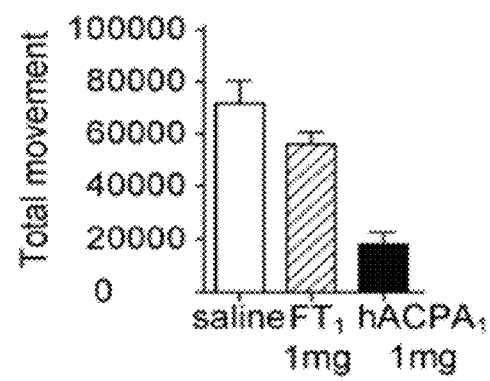
Figure 1I:
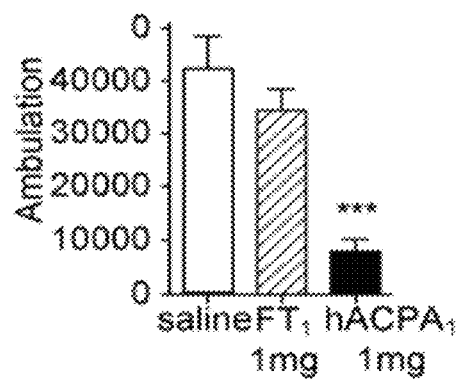

FIG. 1I is a graph showing that zoledronate treatment (100 ug/kg) efficiently prevented the ACPA-induced (hD10/B02 mAb, 1 mg each) increase of CXCL1 mRNA in the ankle joint indicating that there is a link between osteoclast activity and IL-8 upregulation in the joints in vivo.

Figure 12A:
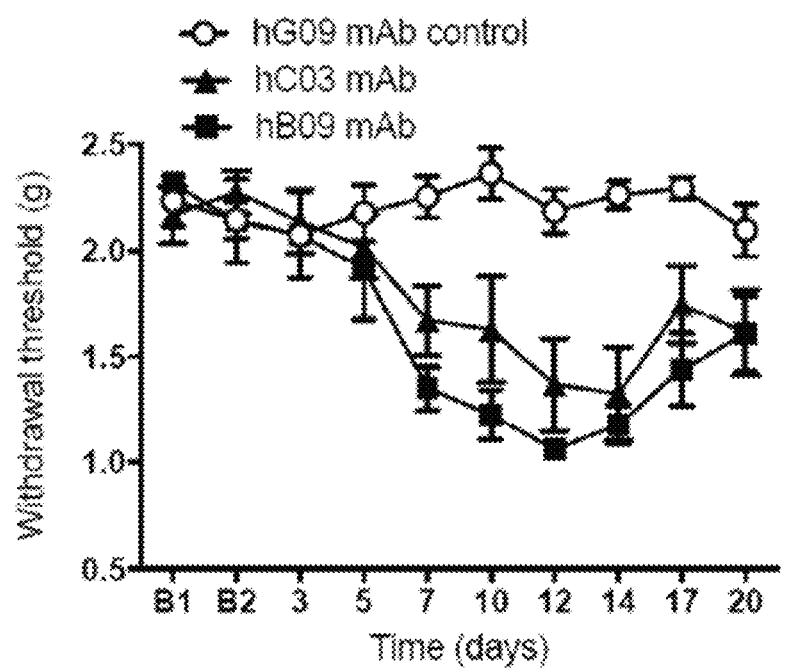
Figure 12B:
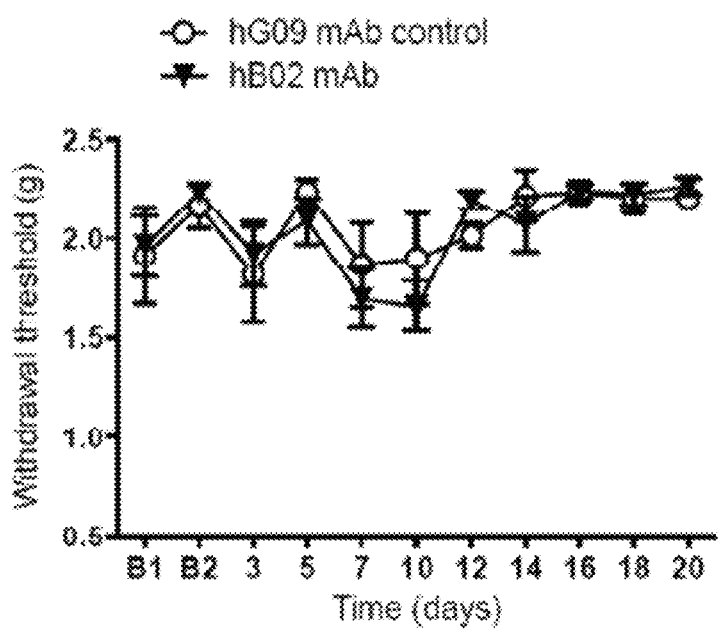
Figure 12C:
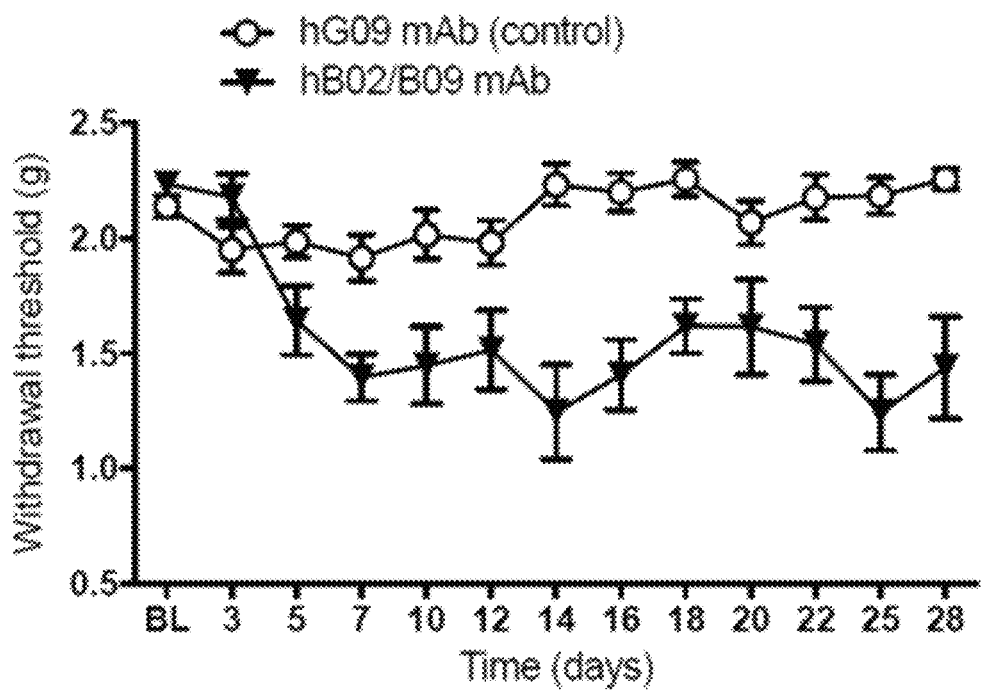
Figure 12D:
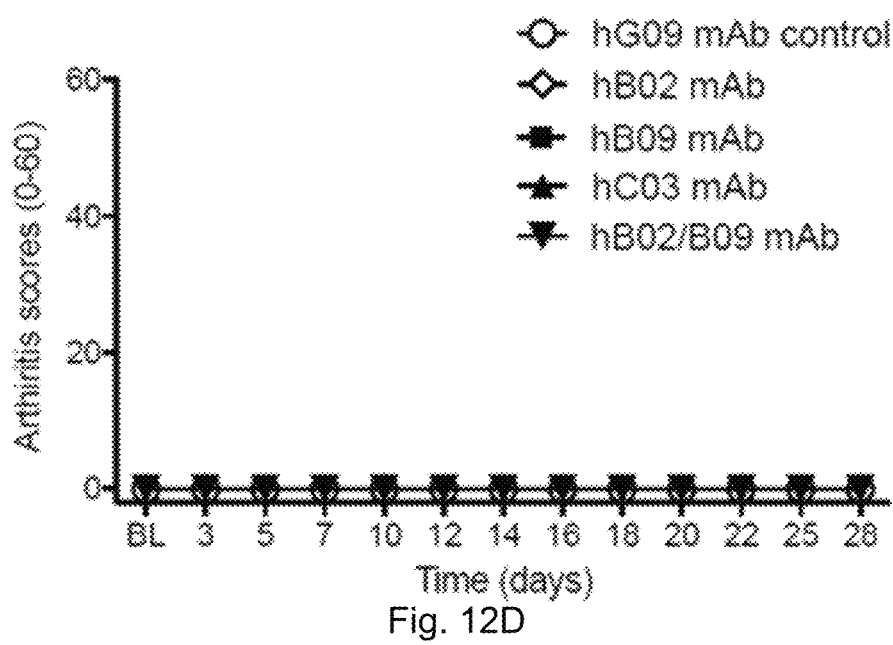

FIGS. 12A-12D depict that human monoclonal ACPAs with different characteristics might differ in their pain-inducing capacity, and that mixing ACPA also induce pain-behavior in animals. The hC03, hB02 and hB09 are IgG2a cloned from single synovial B cells from human RA patients with varying reactivities for major citrullinated epitopes in RA. Without any sign of arthritis (FIG. 12D), 2 mg of the hB09 and hC03 mAb increased mechanical sensitivity (FIG. 12A) while the same amount of hB02 and the control antibody hG09 (FIGS. 12A and 12B), did not. However, mixing the hB09 and hB02 (1 mg each) gave rise to mechanical hypersensitivity lasting for at least 28 days (FIG. 12C). This suggests that fine specificity and possibly also affinities of ACPAs are important for their pain-inducing capacity, and that they may contribute to pain in a synergistic fashion.

Figure 13:
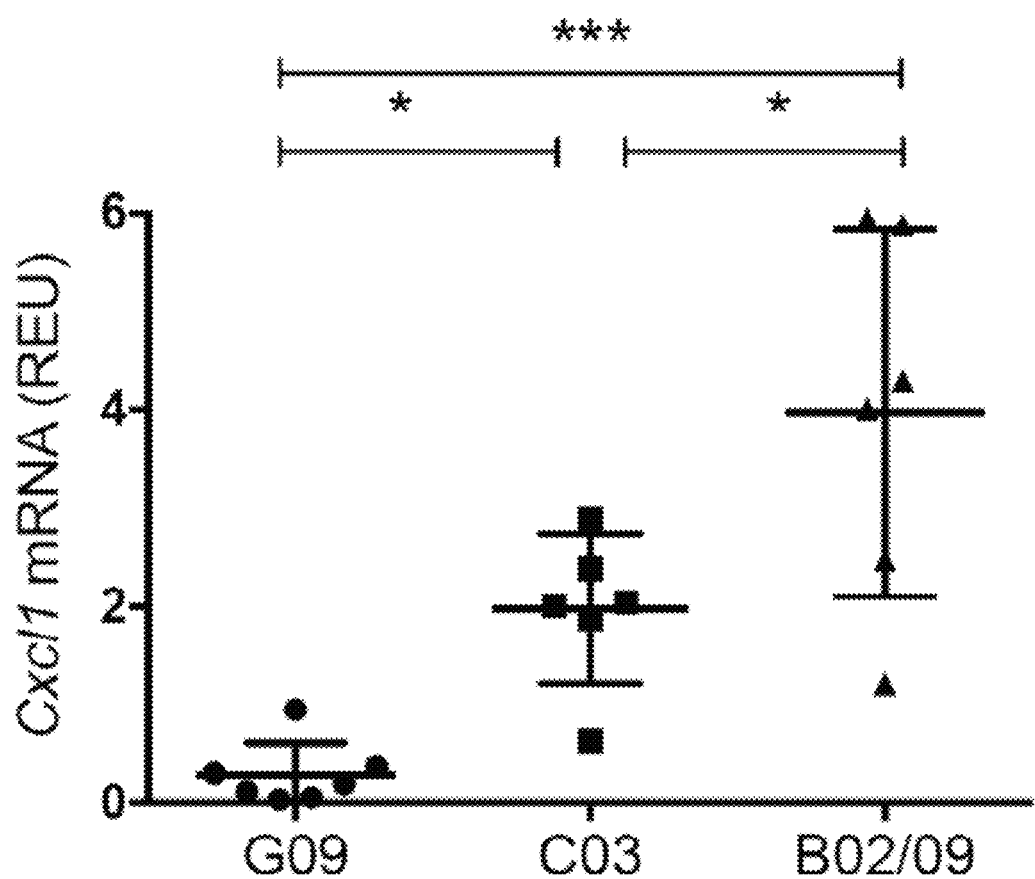

FIG. 13 shows that systemic injection of the human monoclonal ACPA C03 and the combination of the human monoclonal ACPA B02 and B09 lead to an increase of the IL-8 analog CXCL1 mRNA in ankle joints of mice 28 days after injection in comparison to injection of the control antibody G09. (REU=relative expression units).

DESCRIPTION OF EMBODIMENTS

Before the present invention is described, it is to be understood that the terminology employed herein is used for the purpose of describing particular embodiments only and is not intended to be limiting, since the scope of the present invention will be limited only by the appended claims and equivalents thereof.

It must be noted that, as used in this specification and the appended claims, the singular forms "a," "an," and "the" include plural referents unless the context clearly dictates otherwise.

The terms "treatment", "therapy", "therapeutic use", "medicament" and "medical use" encompass both human and animal or veterinary applications. Further, the term treatment is intended to include prevention of the outbreak of symptoms such as bone loss and/or pain, the prevention of the recurrence of such symptoms, as well as the alleviation of such symptoms.

The term "elevated" as in "elevated expression of IL-8" denotes an increase compared to levels measured for the same patient at an earlier occasion, or levels representative for healthy controls, and/or an increase compared to average levels determined for a relevant group of patients or healthy subjects. A person skilled in the art will understand the meaning of the term "elevated" as such as person, e.g. a physician, is well familiar with features characteristic for a general, healthy population, for different populations, and for subjects suffering from a disease but with different severity. Such a skilled person will recognize when a feature deviates, and it is immediately recognized if this deviation represents an increased or elevated value, or a reduced, lowered value.

The terms "contribute" and "contribution" as in "the pain is associated with the contribution of IL-8 and osteoclasts" and other expressions in this description and claims, are intended to cover all interaction and dependencies between for example IL-8 and the perception of pain.

The term "inhibition or blockade" is used to describe an inhibition of a significant part of the action of IL-8 and the activation of osteoclasts, distinguished from a total blocking of this action. It is contemplated that an inhibition or blockade of the action of IL-8 is preferable to a total blocking of the same, considering that IL-8 has many functions in the innate immune response. As briefly summarized above, the present description concerns methods and compounds for the prevention and/or alleviation of pain and/or bone loss where IL-8 and/or osteoclasts contribute, in other words where there is an action or effect of IL-8 and/or the activation of osteoclasts in a subject, i.e. in situations where IL-8 and/or osteoclasts contribute to the pain and/or bone loss.

One group of diseases exhibiting both these features is autoimmune diseases, in which both pain and bone loss are serious consequences of the disease. Rheumatoid arthritis, osteoarthritis and arthralgias of different etiology can be mentioned as examples. Another group of diseases are virus-induced arthralgias, which are associated with high serum levels of IL-8 and osteoclastogenesis.

In order to increase the understanding of what is driving pain in individuals with autoimmunity (including autoantibodies) in more general terms and in particular in individuals at risk for arthritis and with arthritis, and to decipher the role of antibodies in this process, the present inventors have focused on autoantibodies against proteins modified by citrullination, the so-called anti-citrullinated proteins antibodies (ACPA) (Schellekens, G. A., et al., 1998). These autoantibodies are detected in approximately two thirds of all patients with rheumatoid arthritis (RA) and are in addition present in many individuals who do not have joint inflammation, but who are at an increased risk of developing RA in the future. Recent reports show that autoantibodies such as ACPA predate the onset of RA by years (Rantapää-Dahlqvist et al., 2003; Bos, W. H. et al., 2010). Many individuals with ACPAs but without synovitis seek medical attention because of arthralgia (joint pain) without inflammation in joints. Many patients also seek medical help because of arthralgia that persists after successful treatment of the inflammation (Lee, Y. C. et al., 2011).

One object of the present invention is thus to find novel methods and compounds for the alleviation of pain in autoimmune diseases, in particular in subjects exhibiting autoantibodies but not exhibiting the clinical signs of an autoimmune disease, and more specifically subjects with or without arthritis who have antibodies against citrullinated protein antigens and suffer from pain and in patients where inflammation and disease activity has diminished but pain persists. Another object of the present invention is the identification of mechanisms that are responsible for production of a major molecule causing pain, i.e. interleukin 8 (IL-8), from osteoclasts after binding of autoantibodies, including ACPAs, to these osteoclasts. Another object is to develop a diagnostic method and test for identifying patients that would benefit from such treatment.

Another object is to investigate the possibility to use the same compounds, including agents that suppress the action of IL-8, as used for the alleviation of pain, also for the treatment, alleviation or prevention of bone loss, via the inhibition or blockade of osteoclast activation. This inhibition or blockade is relevant both in the context of autoantibody-mediated stimulation of osteoclasts and in other states of osteoclast activation, including bone loss, bone destruction, osteoporosis, and osteopenia. Bone loss occurs in many different diseases and as a result of different conditions, such as autoimmune diseases, e.g. rheumatoid arthritis, lupus, multiple sclerosis, and ankylosing spondylitis; as a consequence of gastrointestinal disorders, e.g. vitamin deficiencies, celiac disease, Crohn's disease and ulcerative colitis; gastrointestinal bypass procedures; endocrine and hormonal disorders, e.g. hyperparathyroidism, hyperthyroidism, diabetes, disorders reflected as deviations in testosterone and/or estrogen levels; hematologic disorders, e.g. leukemia, multiple myeloma, different cancers, including metastases to bone, sickle cell disease; AIDS/HIV, and other chronic diseases. Again, an object is to develop a diagnostic method and test for identifying patients that would benefit from such treatment However, in many cases, bone loss is not a symptom of the disease itself, but rather a side-effect of the disease such as malnutrition or disturbed hormonal levels, or it can even be a side-effect of the medication, for example a side-effect of androgen deprivation therapy in the treatment of prostate cancer, or a side-effect of steroid medications in the treatment of autoimmune diseases.

One example of bone loss is periodontitis, which can be caused by infection and/or inflammation in the gums, tumors in the jaws, as a result of general osteoporosis, or as a side-effect of medication or nutritional deficiencies as exemplified above.

The inventors have now demonstrated that disease associated autoantibodies, such as ACPAs after parenteral administration to otherwise healthy mice induce long-lasting nociceptive (pain-like) behavior, without generating any signs of inflammation.

The inventors also demonstrated that the pain-like behavior in mice after parenteral administration of ACPAs is mediated by the chemokine IL-8. Thus, injection of IL-8 into joints induces pain, and specific blockade of IL-8 receptors alleviates the pain. In separate experiments, it has been shown that osteoclasts release IL-8 after binding of ACPAs. It was shown that parenteral administration of ACPAs induced expression of mRNA coding for IL-8 in the joints of the injected mice, and that both IL-8 production and pain-like behavior occurs without any presence of joint inflammation.

Importantly, the inventors have shown that blockade of IL-8 receptors with specific receptor blockade (for example using reparixin) also blocks the activation of osteoclasts, and thus that blockade of the actions of IL-8 profoundly alters the behavior of osteoclasts, both concerning the release of IL-8 and its effects concerning bone destruction and osteopenia, and concerning the effects of IL-8 on pain. The invention therefore includes both the potential to prevent or alleviate osteopenia and bone destruction via the inhibition or blocking of the action of IL-8, in particular when osteoclasts are stimulated with autoantibodies such as ACPAs, and the potential to inhibit or alleviate pain using IL-8 inhibition or blockade.

Thus, based on the findings presented herein, it is contemplated that the inhibition or blocking of the action of IL-8 is useful in the prevention or alleviation of pain, and in particular pain associated with bone and/or joints.

Consequently the present disclosure makes available, according to a first aspect, a method of preventing and/or alleviating pain in a subject wherein said pain is associated with the contribution of IL-8 and osteoclasts in said subject, wherein an effective amount of a compound is administered to said subject, said compound being capable of inhibiting or blocking the action of IL-8.

According to an embodiment of said first aspect, said compound I compound is a CXCR1/2 antagonist. Preferably, said compound is an allosteric CXCR1/2 inhibitor, which blocks CXCR1 and/or CXCR2 function by blocking receptor signaling instead of chemokine binding.

More preferably said compound is chosen from the compounds exemplified in Table 1 below:

TABLE 1

Examples of CXCR1/2 antagonists

| Tradename, synonym | IUPAC-name |
| --- | --- |
| Reparixin, repertaxin, DF 1681Y | (2R)-2-[4-(2-methylpropyl)phenyl]-N-methylsulfonylpropanamide |
| DF 2162 | 4-[(1R)-2-amino-1-methyl-2-oxoethyl]phenyl trifluoromethane sulfonate |
| AZD8309 | 5-[[(2,3-Difluorophenyl)methyl]thio]-7-[[(1R)-2-hydroxy-1-methylethyl]amino]-thiazolo[4,5-d]pyrimidin-2(3H)-one |
| AZD5069 | N-[2-[[(2,3-difluropheny)methyl]thio]-6-{[(1R,2S)-2,3-dihydroxy-1-methylpropyl]oxy}-4-pyrimidinyl]-1-azetidinesulfonamide |
| PD0220245 | N-(3-[2,20]bithiophenyl-5-yl-6,7-dichloroquinoxalin-2-yl)-N,N-diethyl-butane-1,4-diamine•dihydrochloride. |
| SB-332235 | 1-(4-chloro-2-hydroxy-3-sulfamoylphenyl)-3-(2,3-dichlorophenyl)urea |
| SCH-527123, Navarixin | 2-hydroxy-N,N-dimethyl-3-[[2-[[(1R)-1-(5-methylfuran-2-yl)propyl]amino]-3,4-dioxocyclobuten-1-yl]amino]benzamide |
| SB-656933, Elubrixin | 1-(2-chloro-3-fluorophenyl)-3-(4-chloro-2-hydroxy-3-piperazin-1-ylsulfonylphenyl)urea |
| SB-225002 | N-(2-chloro-3-fluorophenyl)-N'-[4-chloro-2-hydroxy-3-(piperazin-1-ylsulfonyl) phenyl]-urea |

TABLE 1-continued

Examples of CXCR1/2 antagonists

| Tradename, synonym | IUPAC-name |
| --- | --- |
| GSK1325756, Danirixin | 1-[4-chloro-2-hydroxy-3-[(3S)-piperidin-3-yl]sulfonylphenyl]-3-(3-fluoro-2-methylphenyl)urea |

According to a specific embodiment of said first aspect said compound is repartaxin (repertaxin, (2R)-2-[4-(2-methylpropyl)phenyl]-N-methylsulfonylpropanam ide).

Reparixin, (2R)-2-[4-(2-methylpropyl)phenyl]-N-methylsulfonyl propanamide, formerly known as repertaxin, is a non-competitive allosteric inhibitor of CXCR1/2 available from Dompé Farmaceutici, Milano, Italy. Reparixin is currently undergoing clinical trials for example involving adult type 1 diabetes patients undergoing autologous islet cell transplantation, and in combination with chemotherapy with weekly paclitaxel in patients with HER-2 negative metastatic breast cancer.

According to another specific embodiment of said first aspect said compound is danirixin (1-[4-chloro-2-hydroxy-3-[(3S)-piperidin-3-yl]sulfonylphenyl]-3-(3-fluoro-2-methylphenyl)urea.

GSK1325756 (danirixin) is a small molecule, non-peptide, high affinity, selective, and reversible CXCR2 antagonist. The IUPAC name is 1-[4-chloro-2-hydroxy-3-[(3S)-piperidin-3-yl]sulfonylphenyl]-3-(3-fluoro-2-methylphenyl)urea. Danirixin has been evaluated in Phase 2 clinical trials for the treatment of acute uncomplicated influenza, and for inhibition of CD11b cell surface expression, and is currently undergoing trials for treatment of COPD.

Related compounds, such as DF 2162 (4-[(1R)-2-amino-1-methyl-2-oxoethyl]phenyl trifluoromethane sulfonate) (Dompé Farmaceutici, Milano, Italy) is capable of inhibiting both CXCR1 and CXCR2. DF2162 has shown promising results on inflammation in pre-clinical studies of adjuvant-induced polyarthritis and bleomycin-induced pulmonary inflammation and fibrosis, but is yet to be assessed in clinical trials.

Another example, AZD-8309 (5-[[(2,3-Difluorophenyl)methyl]thio]-7-[[(1R)-2-hydroxy-1-methylethyl]amino]-thiazolo[4,5-d]pyrimidin-2(3H)-one), is a fused pyrimidine series-based CXCR2-selective antagonists (originally developed by AstraZeneca R&D, Lund, Sweden) used in phase I clinical trials for COPD and phase II for rheumatoid arthritis and found to be well tolerated.

Another compound, AZD5069 (N-[2-[[(2,3-difluoropheny)methyl]thio]-6-{[(1R,2S)-2,3-dihydroxy-1-methylpropyl]oxy}-4-pyrimidinyl]-1-azetidinesulfonamide) is a CXCR2 receptor antagonist (AstraZeneca R&D, Lund, Sweden). AZD5069 has been entered into phase II studies for indications including COPD, bronchiectasis and asthma.

SB225002 (N-(2-chloro-3-fluorophenyl)-N'-[4-chloro-2-hydroxy-3-(piperazin-1-ylsulfonyl) phenyl]-urea) is a phenol-containing diarylurea small molecule antagonist with more than 150 fold selectivity for CXCR2 over CXCR1 (GlaxoSmith Kline (GSK)). SB225002 is sold for research purposes by R&S Systems under agreement from GSK.

Insertion of a sulfonamide group into the phenol ring of SB656933 was shown to improve the pharmacokinetic properties of SB225002. The resulting compound SB656933 (N-(2-bromophenyl)-N'-(2-hydroxy-4-nitrophenyl)urea) is a CXCR2 antagonist with the same potency as SB225002. SB656933 has been used in a clinical study to reduce ozone-induced airway inflammation in humans, and was found to be well tolerated at all doses. SB656933 is currently sold for research purposes by R&S Systems under agreement from GSK.

PD0220245 (N-(3-[2,20]bithiophenyl-5-yl-6,7-dichloroquinoxalin-2-yl)-N,N-diethyl-butane-1,4-diamine.dihydrochloride) is a CXCR1/2 receptor antagonist available from Axon Medchem BV.

SCH527123 [2-hydroxy-N,N-dimethyl-3-[[2-[[1(R)-(5-methyl-2-furanyl)propyl]amino]-3,4-dioxo-1-cyclobuten-1-yl]amino]benzamide], a potent intracellular allosteric CXCR1/2 antagonist. Clinical trials found oral SCH527123 to be safe and well tolerated and showed a reduction in sputum neutrophils and a modest improvement in severe asthma, while no treatment-induced adverse events were observed. This compound is available from Med Chem Express.

According to another embodiment of said first aspect, said compound is an anti-IL-8 antibody or an antibody capable of reacting with CXCR1/2.

Preferably this is an antibody capable of binding to IL-8 and to inhibit IL-8 function (and IL-8 mediated effects) by blocking IL-8 binding to its receptor for the treatment of pain. For example, this antibody is preferably an antibody capable of inhibiting pro-inflammatory and angiogenic effects induced by IL-8, such as IL-8 induced chemotactic activity for leukocytes and IL-8 induced calcium flux. The antibody can also inhibit IL-8 induced increased expression of CDIIb (Mac-1) and decreased expression of L-selectin (CD62L).

More preferably said antibody is an isolated human monoclonal antibody which binds to human IL-8, comprising the six CDR sequences VLCDR1 of SEQ ID NO: 3, VLCDR2 of SEQ ID NO: 4, VLCDR3 of SEQ ID NO: 5, VHCDR1 of SEQ ID NO: 6, VHCDR2 of SEQ ID NO: 7 and VH CDR3 of SEQ ID NO: 8.

Said antibody is preferably an antibody as defined above, which further comprises a variable heavy chain amino acid sequence as set forth in SEQ ID NO: 2 and/or a variable light chain amino acid sequence as set forth in SEQ ID NO: 1.

More preferably the antibody is selected from an IgG1, an IgG2, an IgG3, an IgG4, an IgM, an IgA1, an IgA2, a secretory IgA, an IgD and an IgE antibody. Still more preferably the antibody is an IgG 1,κ or IgG 1,λ isotype or, alternatively, said antibody is an IgG4,κ or IgG4,λ isotype. More preferably, said antibody comprises an IgG I or IgG3 heavy chain.

Preferably said antibody has one or more of the following characteristics:
(i) inhibits IL-8 binding to its receptors (CXCR1 and CXCR2);
(ii) inhibits IL-8 induced pro-inflammatory effects;
(iii) inhibits IL-8 induced chemotactic activity for neutrophils;
(iv) inhibits IL-8 induced calcium flux;
(v) inhibits IL-8 induced changes in expression levels of adhesion molecules or neutrophils;
(vi) inhibits IL-8 induced increased expression of CD11b (Mac-1) and inhibits IL-8 induced decreased expression of L-selectin on neutrophils;
(vii) does not cross-react with related chemokines selected from human GRO-α, human GRO-β, human IP-10 and human NAP-2;
(viii) significantly inhibits chemotaxis induced by biological fluids which contain multiple chemotactic factors including IL-8.

Examples of suitable antibodies include, but are not limited to ABX-IL8, a fully humanized monoclonal anti-CXCL8 antibody produced by Abgenix, and HuMax®-IL8, a high affinity fully human antibody developed by GenMab A/S, and directed towards IL-8.

ABX-IL8 is a fully humanized monoclonal anti-CXCL8 antibody produced by Abgenix. ABX-IL8 has been assessed in clinical trials for rheumatoid arthritis, psoriasis and chronic obstructive pulmonary disease. Infusions of ABX-IL-8 were found to be well tolerated, with no significant differences in health status or adverse events between treatment and placebo groups.

HuMax®-IL8, a high affinity fully human antibody developed by GenMab A/S, and directed towards IL-8. HuMax-IL8 is currently in clinical development for the treatment of solid tumors under an agreement with Cormorant Pharmaceuticals.

Most preferably said antibody is HuMax®-IL8.

According to an embodiment, freely combinable with any of the aspects and embodiments presented herein, said compound is administered systemically. Systemic administration includes enteral and parenteral routes of administration, well known to persons skilled in the art. Examples of enteral routes of administration include oral, rectal and sublingual administration. Examples of parenteral routes of administration include intravenous, intramuscular, and subcutaneous administration. Other routes of administration, suitable depending on the composition of the final drug based on the findings in this disclosure, include intra articular, topical, transdermal, nasal, intratracheal, intraventricular, and intrapulmonar administration.

According to a second aspect, the inventors make available a method of preventing and/or alleviating pain in a subject wherein said pain is associated with the contribution of IL-8 and osteoclasts in said subject, wherein the presence of IL-8 and activation of osteoclasts is associated with the presence of autoantibodies in said subject, wherein an effective amount of a compound capable of inhibiting or blocking the action of IL-8 is administered to said subject.

Said autoantibodies preferably comprise or consist predominantly of anti-citrullinated protein antibodies (ACPA) and/or antibodies cross-reacting with targets of ACPAs. More preferably, said autoantibodies are anti-citrullinated protein antibodies (ACPA). Thus, according to an embodiment of said second aspect, said autoantibodies are anti-citrullinated protein antibodies (ACPA).

A normal value of ACPA is about 20 EU/ml or less, whereas a level in the range of about 20 to about 39 EU/ml is considered weakly positive, or weakly elevated, about 40 to about 59 EU/ml is considered moderately positive or moderately elevated, whereas above 60 EU/ml is considered strongly positive, or strongly elevated. There are of course individual and genetic variations, but a treating physician will be able to determine if a given patient exhibits elevated levels of ACPA. Importantly, there are indications that the effects of ACPAs and of other antibodies may be further enhanced if also rheumatoid factors (RF) are present.

The term rheumatoid factor and factors (abbreviated RF) collectively refers to antibodies directed against the Fc fragment of immunoglobulin G (IgG). They are heterogeneous and usually composed of immunoglobulin M (IgM). RFs are used as a marker in individuals with suspected rheumatoid arthritis (RA) or other autoimmune conditions, and there are commercially available assays for the detection of RFs, mainly IgM.

The normal reference range for RF is considered to be less than 15 IU/mL. Consequently, and applicable to all embodiments listed in the disclosure, including the examples and claims, the presence of autoantibodies in combination with RFs is a potential marker both in the identification of patients that are likely to benefit from the treatments disclosed herein, and a marker for observing the effects of a drug, and/or the progression/remission of a disease.

According to an embodiment of said second aspect, said autoantibodies are detectable in a sample taken from said patient, but wherein the patient does not manifest clinical signs of an autoimmune disease.

According to a specific embodiment of said second aspect, said autoimmune disease is chosen from rheumatoid arthritis, osteoarthritis, and arthralgia.

According to an embodiment, freely combinable with the above embodiments of said second aspect, said compound is a CXCR1/2 antagonist.

Preferably said compound is an allosteric CXCR1/2 inhibitor, which blocks CXCR1 and/or CXCR2 function by blocking receptor signalling instead of chemokine binding.

According to another embodiment of said second aspect, said compound is chosen from the compounds exemplified in Table 1 above, incorporated herein by reference.

According to a specific embodiment of said second aspect said compound is reparixin (repertaxin, (2R)-2-[4-(2-methylpropyl)phenyl]-N-methylsulfonylpropanamide).

According to another specific embodiment of said second aspect said compound is danirixin, 1-[4-chloro-2-hydroxy-3-[(3S)-piperidin-3-yl]sulfonylphenyl]-3-(3-fluoro-2-methylphenyl)urea.

According to another embodiment of said second aspect, said compound is an anti-IL-8 antibody or an antibody capable of reacting with CXCR1/2.

Preferably this is an antibody capable of binding to IL-8 and to inhibit IL-8 function (and IL-8 mediated effects) by blocking IL-8 binding to its receptor for the treatment of pain. For example, this antibody is preferably an antibody capable of inhibiting pro-inflammatory and angiogenic effects induced by IL-8, such as IL-8 induced chemotactic activity for leukocytes and IL-8 induced calcium flux. The antibody can also inhibit IL-8 induced increased expression of CDIIb (Mac-1) and decreased expression of L-selectin (CD62L).

More preferably said antibody is an isolated human monoclonal antibody which binds to human IL-8, comprising the six CDR sequences VLCDR1 of SEQ ID NO: 3, VLCDR2 of SEQ ID NO: 4, VLCDR3 of SEQ ID NO: 5, VHCDR1 of SEQ ID NO: 6, VHCDR2 of SEQ ID NO: 7 and VH CDR3 of SEQ ID NO: 8.

Said antibody is preferably an antibody as defined above, which further comprises a variable heavy chain amino acid sequence as set forth in SEQ ID NO: 2 and/or a variable light chain amino acid sequence as set forth in SEQ ID NO: 1.

More preferably the antibody is selected from an IgG1, an IgG2, an IgG3, an IgG4, an IgM, an IgA1, an IgA2, a secretory IgA, an IgD and an IgE antibody. Still more preferably the antibody is an IgG 1,κ or IgG 1,λ isotype or, alternatively, said antibody is an IgG4,κ or IgG4,λ isotype. More preferably, said antibody comprises an IgG I or IgG3 heavy chain.

Preferably said antibody has one or more of the following characteristics:
(i) inhibits IL-8 binding to its receptors (CXCR1 and CXCR2);
(ii) inhibits IL-8 induced pro-inflammatory effects;
(iii) inhibits IL-8 induced chemotactic activity for neutrophils;
(iv) inhibits IL-8 induced calcium flux;
(v) inhibits IL-8 induced changes in expression levels of adhesion molecules or neutrophils;
(vi) inhibits IL-8 induced increased expression of CD11b (Mac-1) and inhibits IL-8 induced decreased expression of L-selectin on neutrophils;
(vii) does not cross-react with related chemokines selected from human GRO-α, human GRO-β, human IP-10 and human NAP-2;
(viii) significantly inhibits chemotaxis induced by biological fluids which contain multiple chemotactic factors including IL-8.

Examples of suitable antibodies include, but are not limited to ABX-IL8, a fully humanized monoclonal anti-CXCL8 antibody produced by Abgenix, and HuMax®-IL8, a high affinity fully human antibody developed by GenMab A/S, and directed towards IL-8.

Most preferably said antibody is HuMax®-IL8.

One aspect of the invention is thus the use of HuMax®-IL8 for preventing and/or alleviating pain in a subject wherein said pain is associated with the contribution of IL-8 and/or osteoclasts in said subject, wherein the action of IL-8 and/or the contribution of osteoclast activity in said subject is/are associated with the presence of autoantibodies in said subject, in particular an elevated level of said autoimmune antibodies.

According to an embodiment, freely combinable with any of the aspects and embodiments presented herein, said compound is administered systemically. Systemic administration includes enteral and parenteral routes of administration, well known to persons skilled in the art. Examples of enteral routes of administration include oral, rectal and sublingual administration. Examples of parenteral routes of administration include intravenous, intramuscular, and subcutaneous administration. Other routes of administration, suitable depending on the composition of the final drug based on the findings in this disclosure, include intra articular, topical, transdermal, nasal, intratracheal, intraventricular, and intrapulmonar administration.

Another aspect relates to a diagnostic method and/or a diagnostic kit for identifying individuals that would benefit from the above mentioned treatment, the alleviation or prevention of pain, wherein said method and/or kit comprises one or more of the following steps or components:
    an assay for determining the level of IL-8 in serum;
    an assay for determining the level of IL-8 in synovial fluid;
    an assay for determining increased production of Il-8 from osteoclasts;
    an assay for determining the presence and identity of autoantibodies, including presence of antibodies to citrullinated antigens and/or rheumatoid factors (RF); and
    a questionnaire for quantitatively and optionally qualitatively assessing pain, and in particular joint pain (arthralgia).

According to a particular embodiment, said kit further comprises means for qualitatively or quantitatively assessing bone density and/or the degree of bone loss.

Methods and assays for the determination of the level of IL-8 in a sample are well known to persons skilled in the art. There are for example commercially available cytokine biochip arrays using sandwich and competitive chemiluminescence immunoassays. Serum levels of IL-8 of 7.5 pg/ml have been reported for patients diagnosed with RA, compared to levels around 3.5 pg/ml measured in healthy. The IL-8 levels in synovial fluid are correspondingly higher, as high as 8000 pg/ml in RA patients, and up to approximately 2000 pg/ml in osteoarthritis.

Assays for the qualitative and quantitative analysis of antibodies are also available, for example the cyclic citrullinated peptide (CCP) antibody test. One commercially available CCP test is the Immunoscan CCPlus®, supplied by Euro Diagnostica AB, Malmö, Sweden. This is an enzyme-linked immunosorbent assay (ELISA) for qualitative and semi-quantitative determination of IgG antibodies to Cyclic Citrullinated Peptides (CCP) in human sera. This assay recognizes both antibodies (ACPAs) able to activate osteoclasts and induce IL-8 production and other ACPAs not able to activate osteoclasts and induce Il-8 production. Therefore this assay is useful but not optimal for identifying patients at risk of developing pain and/or bone loss as well as at risk of developing RA or other autoimmune disease. The inventors are currently using a modified high sensitivity and fine specificity ACPA test based on a multiplex fluorescent detection assay which enables the inventors to specifically identify specific anti-citrulline antibodies (ACPAs) with potential to active osteoclasts, and to induce IL-8 production from osteoclasts, and to cause pain that is dependent on production of IL-8 from osteoclasts.

Similarly, the inventors are currently using a questionnaire and visual pain assessment tool.

Another aspect relates to a method for identifying individuals that would benefit from treatment according to any one of above aspects and embodiments, wherein said method comprises one or more of the following steps:
  determining the level of IL-8 in serum,
  determining the level of IL-8 in synovial fluid,
  determining the presence of an increased production of IL-8 from osteoclasts
  determining the presence and identity of autoantibodies, including presence of antibodies to citrullinated antigens and/or the presence of rheumatoid factors (RF), and
  quantitatively and optionally qualitatively assessing pain.

Preferably said method further comprises a step of qualitatively or quantitatively assessing bone density and/or the degree of bone loss.

Based on the findings presented herein, it is contemplated that inhibition or blockade of the action of IL-8 and the consequent inhibition or inhibition or blockade of osteoclast activation is also useful for the prevention, alleviation or treatment of bone loss.

The present disclosure makes available, according to a further aspect, a method of preventing and/or alleviating bone loss associated with the action of IL-8 and/or the contribution of osteoclast activity in said subject, wherein an effective amount of a compound capable of inhibiting or blocking the action of IL-8 is administered to said subject.

According to an embodiment of said aspect, said compound is a CXCR1/2 antagonist. According to another embodiment, said compound is an allosteric CXCR1/2 inhibitor, which blocks CXCR1 and/or CXCR2 function by blocking receptor signaling instead of chemokine binding.

Preferably said compound is again chosen from the compounds of Table 1, incorporated herein by reference.

More preferably said compound is reparixin (repertaxin, (2R)-2-[4-(2-methylpropyl)phenyl]-N-methylsulfonylpropanam ide). Reparixin, (2R)-2-[4-(2-methylpropyl)phenyl]-N-methylsulfonyl propanamide, formerly known as repertaxin, is a non-competitive allosteric inhibitor of CXCR1/2 available from Dompé Farmaceutici, Milano, Italy. Reparixin is currently undergoing clinical trials for example involving adult type 1 diabetes patients undergoing autologous islet cell transplantation, and in combination with chemotherapy with weekly paclitaxel in patients with HER-2 negative metastatic breast cancer.

Related compounds, such as DF 2162 (4-[(1R)-2-amino-1-methyl-2-oxoethyl]phenyl trifluoromethane sulfonate) (Dompé Farmaceutici, Milano, Italy) is capable of inhibiting both CXCR1 and CXCR2. DF2162 has shown promising results in pre-clinical studies of adjuvant-induced polyarthritis and bleomycin-induced pulmonary inflammation and fibrosis, but is yet to be assessed in clinical trials.

Another example, AZD-8309, is a fused pyrimidine series-based CXCR2-selective antagonists (AstraZeneca R&D, Lund, Sweden) used in phase I clinical trials for COPD and phase II for rheumatoid arthritis and found to be well tolerated.

Another compound, AZD5069 (N-[2-[[(2,3-difluoropheny)methyl]thio]-6-{[(1R,2S)-2,3-dihydroxy-1-methylpropyl]oxy}-4-pyrimidinyl]-1-azetidinesulfonamide) is a CXCR2 receptor antagonist (AstraZeneca R&D, Lund, Sweden). AZD5069 has been entered into phase II studies for indications including COPD, bronchiectasis and asthma.

SB225002 (N-(2-chloro-3-fluorophenyl)-N'-[4-chloro-2-hydroxy-3-(piperazin-1-ylsulfonyl) phenyl]-urea) is a phenol-containing diarylurea small molecule antagonist with more than 150 fold selectivity for CXCR2 over CXCR (GlaxoSmithKline (GSK)). SB225002 sold for research purposes by R&S Systems under agreement from GSK.

Insertion of a sulfonamide group into the phenol ring of SB656933 was shown to improve the pharmacokinetic properties of SB225002. The resulting compound SB656933 (N-(2-bromophenyl)-N'-(2-hydroxy-4-nitrophenyl)urea) is a CXCR2 antagonist with the same potency as SB225002. SB656933 has been used in a clinical study to reduce ozone-induced airway inflammation in humans, and was found to be well tolerated at all doses. SB656933 sold for research purposes by R&S Systems under agreement from GSK.

PD0220245 (N-(3-[2,20]bithiophenyl-5-yl-6,7-dichloro-quinoxalin-2-yl)-N,N-diethyl-butane-1,4-diamine.dihydrochloride) is a CXCR1/2 receptor antagonist available from Axon Medchem BV.

SCH527123 [2-hydroxy-N,N-dimethyl-3-[[2-[[1(R)-(5-methyl-2-furanyl)propyl]amino]-3,4-dioxo-1-cyclobuten-1-yl]amino]benzamide], a potent intracellular allosteric CXCR1/2 antagonist. Clinical trials found oral SCH527123 to be safe and well tolerated and showed a reduction in sputum neutrophils and a modest improvement in severe asthma, while no treatment-induced adverse events were observed. The compound is available from Med Chem Express.

GSK1325756 (danirixin) is a small molecule, non-peptide, high affinity, selective, and reversible CXCR2 antagonist. The IUPAC name is 1-[4-chloro-2-hydroxy-3-[(3S)-piperidin-3-yl]sulfonylphenyl]-3-(3-fluoro-2-methphenyl) urea. Danirixin has been evaluated in Phase 2 clinical trials for the treatment of acute uncomplicated influenza, and for inhibition of CD11b cell surface expression, and is currently undergoing trials for treatment of COPD.

ABX-IL8 is a fully humanized monoclonal anti-CXCL8 antibody produced by Abgenix. ABX-IL8 has been assessed in clinical trials for rheumatoid arthritis, psoriasis and chronic obstructive pulmonary disease and infusions of ABX-IL-8 found to be well tolerated, with no significant differences in health status or adverse events between treatment and placebo groups.

According to another embodiment of said aspect, said compound is an anti-IL-8 antibody or an antibody reactive with CXCR1/2.

According to a preferred embodiment of said aspect, the action of IL-8 and/or the contribution of osteoclast activity in said subject is/are associated with the presence of autoantibodies in said subject. In this embodiment, said autoantibodies preferably comprise or consist predominantly of anti-citrullinated protein antibodies (ACPA) and/or antibodies cross-reacting with targets of ACPAs. More preferably, said autoantibodies are anti-citrullinated protein antibodies (ACPA).

A normal value of ACPA is about 20 EU/ml or less, whereas a level in the range of about 20 to about 39 EU/ml is considered weakly positive, or weakly elevated, about 40 to about 59 EU/ml is considered moderately positive or moderately elevated, whereas above 60 EU/ml is considered strongly positive, or strongly elevated. There are of course individual and genetic variations, but a treating physician will be able to determine if a given patient exhibits elevated levels of ACPA. Importantly, there are indications that the effects of ACPAs and of other antibodies may be further enhanced if also rheumatoid factors (RF) are present.

The term rheumatoid factors (abbreviated RFs) collectively refers to antibodies directed against the Fc fragment of immunoglobulin G (IgG). They are heterogeneous and usually composed of immunoglobulin M (IgM). RFs are used as a marker in individuals with suspected rheumatoid arthritis (RA) or other autoimmune conditions, and there are commercially available assays for the detection of RFs, mainly IgM. The normal reference range for RF is considered to be less than 15 IU/mL. Consequently, and applicable to all embodiments listed in the disclosure, including the examples and claims, the presence of autoantibodies in combination with RFs is a potential marker both in the identification of patients that are likely to benefit from the treatments disclosed herein, and a marker for observing the effects of a drug, and/or the progression/remission of a disease.

According to an embodiment, said autoantibodies are detectable in a sample taken from said patient, but wherein the patient does not manifest clinical signs of an autoimmune disease.

According to an embodiment, freely combinable with the above aspects and embodiments, said autoimmune disease is chosen from rheumatoid arthritis, osteoarthritis, and arthralgia.

A sixth aspect is the use of an IL-8 antagonist for the alleviation and/or prevention of bone loss associated with the action of IL-8 and/or the contribution of osteoclast activity in a subject.

According to an embodiment of said sixth aspect, said compound is a CXCR1/2 antagonist. Preferably, said compound is an allosteric CXCR1/2 inhibitor, which blocks CXCR1 and/or CXCR2 function by blocking receptor signaling instead of chemokine binding.

More preferably said compound is chosen from reparixin (repertaxin, (2R)-2-[4-(2-methylpropyl)phenyl]-N-methylsulfonyl propanamide), DF 2162 (4-[(1R)-2-amino-1-methyl-2-oxoethyl]phenyl trifluoromethane sulfonate), AZD-8309, AZD5069 (N-[2-[[(2,3-difluopheny)methyl]thio]-6-{[(1R,2S)-2,3-dihydroxy-1-methylpropyl]oxy]-4-pyrimidinyl]-1-azetidinesulfonamide, SB-332235, SCH527123 (navarixin), SB-656933 (elubrixin) and SB225002 (N-(2-chloro-3-fluorophenyl)-N'-[4-chloro-2-hydroxy-3-(piperazin-1-ylsulfonyl) phenyl]-urea).

Most preferably said compound is reparixin (repertaxin, (2R)-2-[4-(2-methylpropyl)phenyl]-N-methylsulfonyl propanamide).

According to another embodiment of said sixth aspect, said compound is an anti-IL-8 antibody or an antibody reactive with CXCR1/2.

According to a preferred embodiment of this aspect, the action of IL-8 and/or the contribution of osteoclast activity in said subject is/are associated with the presence of autoantibodies in said subject. In this embodiment, said autoantibodies preferably comprise or consist predominantly of anti-citrullinated protein antibodies (ACPA) and/or antibodies cross-reacting with targets of ACPAs. More preferably, said autoantibodies are anti-citrullinated protein antibodies (ACPA).

A normal value of ACPA is about 20 EU/ml or less, whereas a level in the range of about 20 to about 39 EU/ml is considered weakly positive, or weakly elevated, about 40 to about 59 EU/ml is considered moderately positive or moderately elevated, whereas above 60 EU/ml is considered strongly positive, or strongly elevated. There are of course individual and genetic variations, but a treating physician will be able to determine if a given patient exhibits elevated levels of ACPA. Importantly, there are indications that the effects of ACPAs and of other antibodies may be further enhanced if also rheumatoid factors (RF) are present.

The term rheumatoid factors (abbreviated RFs) collectively refers to antibodies directed against the Fc fragment of immunoglobulin G (IgG). They are heterogeneous and usually composed of immunoglobulin M (IgM). RFs are used as a marker in individuals with suspected rheumatoid arthritis (RA) or other autoimmune conditions, and there are commercially available assays for the detection of RFs, mainly IgM. The normal reference range for RF is considered to be less than 15 IU/mL. Consequently, and applicable to all embodiments listed in the disclosure, including the examples and claims, the presence of autoantibodies in combination with RFs is a potential marker both in the identification of patients that are likely to benefit from the treatments disclosed herein, and a marker for observing the effects of a drug, and/or the progression/remission of a disease.

According to an embodiment, said autoantibodies are detectable in a sample taken from said patient, but wherein the patient does not manifest clinical signs of an autoimmune disease.

According to an embodiment, freely combinable with the above aspects and embodiments, said autoimmune disease is chosen from rheumatoid arthritis, osteoarthritis, and arthralgia.

A seventh specific aspect is the use of reparixin for the alleviation and/or prevention of bone loss.

According to an embodiment, freely combinable with any of the aspects and embodiments presented herein, said compound is administered systemically. Systemic administration includes enteral and parenteral routes of administration, well known to persons skilled in the art. Examples of enteral routes of administration include oral, rectal and sublingual administration. Examples of parenteral routes of administration include intravenous, intramuscular, and subcutaneous administration. Other routes of administration, suitable depending on the composition of the final drug based on the findings in this disclosure, include topical, transdermal, nasal, intratracheal, intraventricular, and intrapulmonar administration.

An eight aspect is a diagnostic method and/or a diagnostic kit for identifying individuals that would benefit from the above mentioned treatment, the alleviation or prevention of bone loss, wherein said method and/or kit comprises one or more of the following:

an assay for determining the level of IL-8 in serum,
an assay for determining the level of LI-8 in synovial fluid,
an assay for determining the production of IL-8 from osteoclasts an assay for determining the presence and identity of autoantibodies, an assay for the qualitative or quantitative determination of bone density, and optionally a questionnaire for quantitatively and optionally qualitatively assessing pain, in particular pain associated with joints (arthralgia) or bone (bone pain).

Methods and assays for the determination of the level of IL-8 in a sample are well known to persons skilled in the art. There are for example commercially available cytokine biochip arrays using sandwich and competitive chemiminsecense immunoassays. Serum levels of IL-8 of 7.5 pg/ml have been reported for patients diagnosed with RA, compared to levels around 3.5 pg/ml measured in healthy. The IL-8 levels in synovial fluid are correspondingly higher, as high as 8000 pg/ml in RA patients, and up to approximately 2000 pg/ml in osteoarthritis.

Assays for the qualitative and quantitative analysis of antibodies are also available, for example the cyclic citrullinated peptide (CCP) antibody test. One commercially available CCP test is the Immunoscan CCPlus®, supplied by Euro Diagnostica AB, Malmö, Sweden. This is an enzyme-linked immunosorbent assay (ELISA) for qualitative and semi-quantitative determination of IgG antibodies to Cyclic Citrullinated Peptides (CCP) in human sera. This assay recognizes both antibodies (ACPAs) able to activate osteoclasts and induce IL-8 production and other ACPAs not able to activate osteoclasts and induce Il-8 production. Therefore this assay is useful but not optimal for identifying patients at risk of developing pain and/or bone loss as well as at risk of developing RA or other autoimmune disease. The inventors are currently using a modified high sensitivity and fine specificity ACPA test based on a multiplex fluorescent detection assay which enables the inventors to specifically identify specific anti-citrulline antibodies (ACPAs) with potential to active osteoclasts, and to induce IL-8 production from osteoclasts, and to cause pain that is dependent on production of IL-8 from osteoclasts.

Similarly, the inventors are currently using a questionnaire and visual pain assessment tool.

Bone density can be quantified in different ways, for example measured using ultrasound, dual X-ray absorptiometry (DXA), dual energy X-ray absorptiometry (DEXA), or a special X-ray called quantitative computed tomography (QCT), to mention a few examples.

EXAMPLES

To examine if RA-associated autoantibodies are directly linked to nociception (pain) pain-like behavior in mice was assessed after injection of IgG isolated and pooled from RA-patients or healthy age matched donors. The patients were diagnosed according to the 1987 American College of Rheumatology criteria (Arnett, F. C. et al., 1988) and determined to be ACPA-positive (ACPA+) or ACPA negative (ACPA−) using a routine assay for ACPAs (CCP2 assay). Change in sensitivity to mechanical stimulation was assessed using von Frey-filaments and the up-down method (Chaplan, S. R. et al., 1994). A pronounced drop in tactile thresholds was observed in mice injected with 4 mg IgG from ACPA+RA-patients whereas the same amount of IgG from ACPA− RA patients or healthy individuals did not induce sensitivity to mechanical stimulation (FIG. 1A).

In order to examine if ACPAs are pronociceptive, the IgG antibodies specific for citrullinated antigens were separated using a CCP2 affinity column as previously described (Ossipova, E. et al., 2014), thereby also generating a "flow through" (FT) IgG fraction that contain all non-ACPA IgG8. Three batches (batch 1-3) of ACPA and corresponding FT were prepared, containing IgG from 38, 6, and 25 ACPA+ RA patients respectively. Strikingly, while FT IgG (batch 1, 1 mg) or IgG from healthy individuals (1 mg) injected i.v. did not alter the thresholds for evoking a response to mechanical stimulation, ACPA (batch 1, 1 mg) induced mechanical hypersensitivity within three days (FIG. 1B, C), which lasted for at least 28 days (FIG. 1C).

Figure 1J:
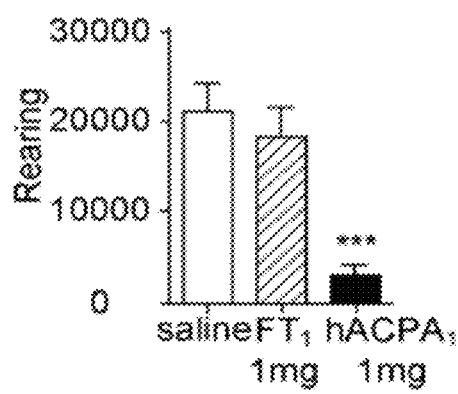
Figure 1K:
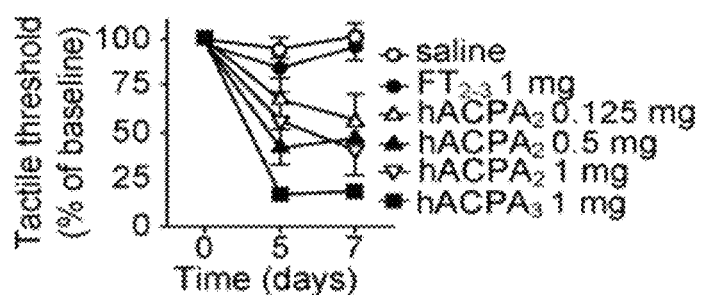
Figure 1L:
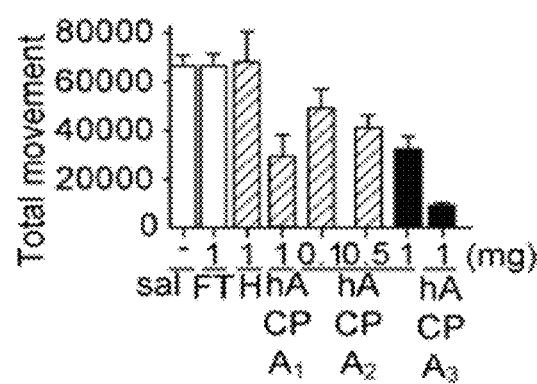
Figure 1M:
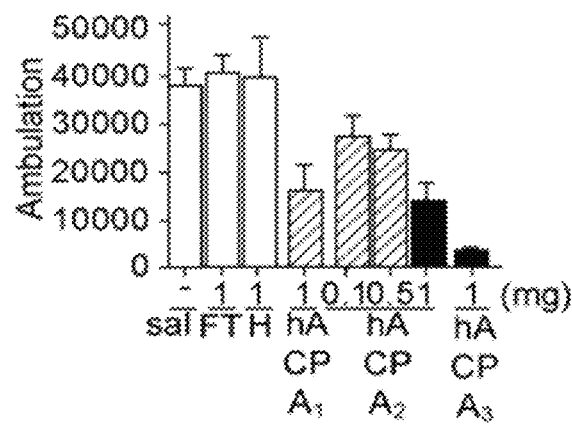
Figure 1N:
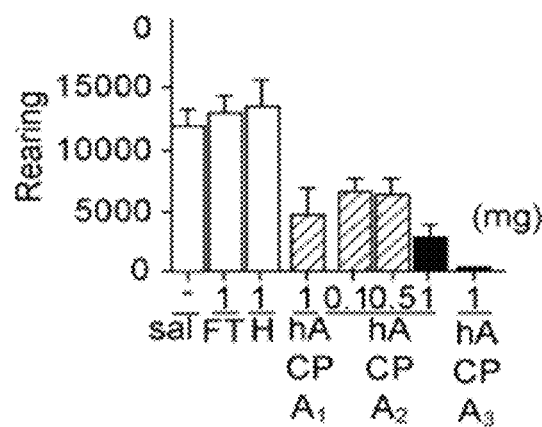

Injected mice were also tested in thermal assays measuring sensitivity to heat and cold, revealing that ACPA injected mice were more sensitive to thermal stimuli than saline or FT injected mice (FIG. 1E-G). In order to expand our assays to not only examine evoked (mechanical and thermal hypersensitivity) but also spontaneous (non-evoked) pain-like behavior, changes in spontaneous locomotor activity were also assessed. By using a comprehensive laboratory animal monitor system (CLAMS, Columbus), total movement, ambulation (directional walking), and rearing was monitored from 18.00-06.00 a clock the night between days 2 and 3. Similar assays have been used successfully to study non-reflexive pain-like behavior in experimental models of pain (Cobos, E. J. et al., 2012). Injection of 1 mg purified ACPA (batch 1), but not 1 mg FT IgG (batch 1), induced a reduction in all movement parameters (FIG. 1H-J). No signs of joint swelling (FIG. 1D) or inflammation-related sickness behavior (piloerection, weight loss, reduced feeding, FIG. 5A-C) were observed between night 2 and 3, thus the reduction in movement is unlikely to be the result of a local or generalized inflammatory event, but rather the consequence of pro-nociceptive actions of ACPA.

Using a different strain of mice, batch 1-3 of ACPA induced evoked and spontaneous pain-like behaviors, in a dose-dependent fashion, while injection of the corresponding batches of FT IgG were without effect (FIG. 1K-N, FIG. 5D). Interestingly, even though all three ACPA batches induced nociceptive behaviors, the potency differed between the different batches. Since the ACPA batches were derived from different patients they will contain a wide spectrum of human antibodies with different fine specificity for various epitopes of citrullinated autoantigens (Ossipova, E. et al., 2014).

In order to get additional information on whether ACPAs with different characteristics might differ in their pain-inducing capacity, monoclonal antibodies targeting varied sets of citrullinated epitopes were used. The D10, B2, and C7 are murinized IgG2a cloned from single synovial B cells from human RA patients (Amara, K. et al., 2013), with varying reactivities for major citrullinated epitopes in RA (FIG. 2A). Interestingly, without any sign of arthritis (FIG. 2B), both the D10 and B2 increased mechanical sensitivity (FIG. 2C-D) while the C7 (FIG. 2C) and E2 (a control human monoclonal specific for tetanus toxin, FIG. 2D) did not. This suggests that fine specificity and possibly also affinities of ACPAs are important for their pain-inducing capacity.

In order to investigate the fate of the injected human antibodies, western blot was used to investigate the localization in various organs obtained from mice 7 days after injection. Presence of these human ACPAs was seen in ankle joint and tibial bone marrow, but not in any part of the CNS (FIG. 3A), suggesting activation of peripheral nociceptive pathways. Certain autoantibodies have the ability to directly activate sensory neurons by binding voltage-gated potassium channels (Klein, C. J. et al., 2012). To investigate if ACPAs have similar capacity primary cultures of dorsal root ganglion neurons were stimulated with ACPA and measured calcium flux and inward current changes, revealing that ACPA does not affect the excitability of neurons directly in any of the tested parameter (Not shown).

Histological sections from ankle joints and tibia were also investigated, but no signs of inflammation, such as cell infiltration, synovial hyperplasia, cartilage destruction, or bone erosion was detected (FIG. 3B-E). To examine other molecular features in the joints and bones after injection of ACPAs, ankle joint mRNA extracts were analyzed using quantitative RT-PCR. No difference in mRNA levels between ACPA and saline injected mice was seen for the chemokines (Cxcl5, Ccl2), cytokines (Tnf, Il1b, Il6), inflammatory enzyme (Cox2), matrix metalloproteases (Mmp 2,9, 13), and mast cell proteases (Mcpt4, Tpsb2). Noteworthy, however, Cxcl1 and Cxcl2 mRNA levels were elevated in ACPA ankle joints (FIG. 3F).

Figure 3G:
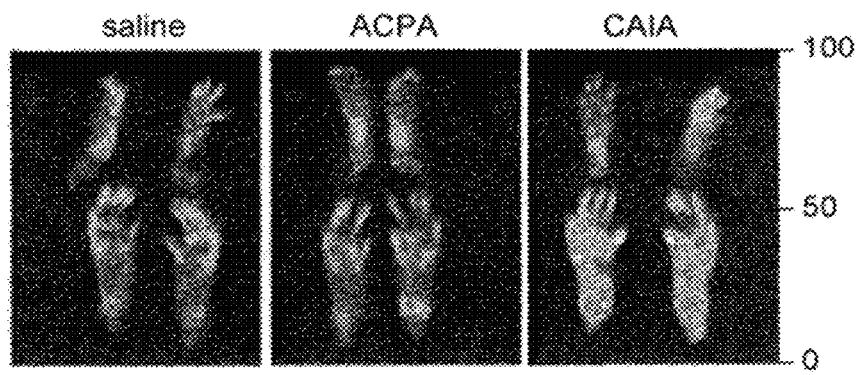

The same factors were also analyzed in the plantar skin from the hind paw, which is the region where the mechanical sensitivity is measured and presence of ACPA was detected with WB. None of the examined factors were elevated in the skin (FIG. 7A). The molecular analysis of joints was extended further by investigating the activity of functional MMPs, by injecting a fluorescent marker that becomes optically active when cleaved by MMPs (Ibarra, J. M., 2011). This marker showed that ACPA does not induce activation of MMPs in the paw (FIG. 3G, FIG. 7B). Taken together, the molecular and histological analyses suggest that the ACPAs used in this study do not themselves cause joint inflammation or direct activation of sensory neurons, but selectively induce an increased production of two closely related chemokines that are functional homologues of human IL-8 (Verri, W. A. et al., 2006).

The CXCL class of chemokines is commonly associated with chemotaxis of leukocytes (Russo, R. C., et al., 2014). Interestingly, CXCL ligands have also been reported to induce nociceptive signal transmission when injected into peripheral tissues of rodents (Cunha, T. M. et al., 2005; Guerrero, A. T. G. et al., 2012), or into the spinal fluid (Zhang, Z.-J. et al., 2013), acting via CXCR2 expressed on peripheral and central nociceptive neurons (Zhang, Z.-J. et al., 2013; Qin, X., et al., 2005; Wang, J.-G. et al., 2008).

To confirm the peripheral nociceptive action of the mouse homologs of IL-8, CXCL1 and CXCL2 was injected into the ankle joint of mice, which produced a rapid onset of mechanical sensitivity in the ipsilateral paw, lasting at least 24 h (FIG. 4A).

ACPAs have been shown to enhance bone loss in RA patients and rodents (Harre, U. et al., 2012). This effect is mediated via direct induction of osteoclast differentiation by ACPA binding to citrullinated epitopes on precursor cells, a process that is detected also in absence of clinical signs of inflammation (Güler-Yüksel, M. et al., 2009). Notably, a recent study in one of the laboratories of the present inventors has shown that IL-8 is released by human osteoclasts in response to ACPA (Krishnamurthy, A. et al., 2016), and IL-8 has also been shown to be a key autocrine factor in osteoclastogenesis (Kopesky, P. et al., 2014). Thus, it is contemplated that the inhibition or blockade of the action of IL-8 is a potent approach to the inhibition or blockade of osteoclast activation.

To test if ACPA drive release of IL-8 analogues also in mouse osteoclasts, CD11b+ cells from bone marrow of mice were cultured in the presence of RANKL and M-CSF. ACPA or FT were added to the cultures at day 6, when multi-nucleated cells (osteoclasts) had started to form, and it was found that ACPA, but not FT, induced significant release of CXCL1 (FIG. 4B) within 4 days of presence of ACPA, while CXCL2 levels (FIG. 4C) and number of osteoclasts (FIG. 8A) did not change. Thus, ACPA is altering osteoclast activity and promoting release of similar chemokines in both human and mouse osteoclasts.

To examine the functional coupling between ACPA, CXCL1 release and nociception in vivo, mice injected with monoclonal ACPA (D10 and B2) were treated with reparixin, a CXCR1/2 receptor antagonist, when ACPA-induced mechanical hypersensitivity had developed. Six consecutive days of reparixin injections partially reversed mechanical and heat hypersensitivity compared to saline controls (FIG. 4C, E) and attenuated sensitivity to cold day 19 (FIG. 8D). Reparixin treatment did not affect tactile thresholds in naive mice that had not been injected with ACPAs (FIG. 8C)

Methods
Animals

Experiments were performed using adult male B10.RIII mice (bred at Department of Medical Biochemistry and Biophysics, Karolinska Institutet) and Balb/c (Harlan) 15-22 weeks of age. Mice were housed in standard cages (3-5 per cage) in a climate controlled environment maintaining a 12-hour light/dark cycle with access to food and water ad libitum. All experiments were approved by the local ethics committee for animal experiments in Sweden (Stockholm Norra Djurförsöksetiska nämnd).

Preparation of Human ACPAs (hACPA, Anti-CCP2 IgG Antibodies)

Purification of IgG from humans was done as described previously (Ossipova et al., 2014). Plasma and serum samples (from ACPA+RA patients, total n=69, ACPA- RA patients, n=5 and healthy controls, n=6) were centrifuged at 3000 g for 5 minutes and diluted 1:5 (v/v) in PBS. IgGs were purified from diluted plasma and sera on HiTrap Protein G HP columns (GE Healthcare), according to the manufacturer's instructions. Eluted IgGs were dialyzed against PBS and the antibodies from ACPA+RA patients were applied to the CCP2 affinity column (kindly provided by Euro-Diagnostica). ACPAs were eluted using 0.1 M glycine-HCl buffer (pH 2.7) and the pH was directly adjusted to 7.4 using 1 M Tris (pH 9). IgG not binding to the CCP2-column were used as control in experiments, denoted as flow through (FT).

Autoantibodies were concentrated and the buffer exchanged to PBS using the 10 kDa Microsep™ UF Centrifugal Device (Pall Life Science). Recovery and purity of total ACPAs were analyzed by SDS-PAGE followed by Coomassie Blue staining and anti-CCP2 reactivity (Immunoscan CCPlus® assay). The concentration (mg/ml) of total IgG was calculated based on the initial plasma/sera volume applied to the Protein G column and the amount of IgG eluted from the column.

The endotoxin levels were determined in the different pools of autoantibodies by the limulus amebocyte lysate assay and the cut-off for positivity was assumed as >0.05 EU/ml. Three different ACPA pools were utilized for the in vivo experiments: ACPA pool 1 containing autoantibodies purified from 38 plasma samples, ACPA pool 2 containing autoantibodies from 6 plasma/sera samples (plasma n=5; serum n=1), and ACPA pool 3 that includes autoantibodies purified from 25 plasma/sera samples (plasma n=15; sera n=10). To prepare the ACPA+ pool, antibodies isolated from the same plasma/sera samples as used for ACPA pool 2 were selected. This pool of antibodies was constituted by ACPA and non-ACPA IgGs.

Generation of Monoclonal ACPA

Murinized monoclonal antibodies (mAbs) D10, B2, C7 and E2 were generated as previously described (Amara, K. et al., 2013).

In brief, single B-cells were sorted from synovial fluid of ACPA+ patients into a 96-well plate. Digested PCR products from each single cell were cloned into expression vectors containing Igγ1, Igκ, or Igλ constant regions and transfected into human embryonic fibroblasts HEK293 (Gibco Invitrogen). Supernatants were collected and purified by binding to protein G-sepharose column (Sigma-Aldrich) and expression of heavy and light chain, as well as purity, was verified by PAGE. Reactivity of the generated monoclonal antibodies against citrullinated and native form of α-enolase (CEP-1), vimentin (aa 60-75), and fibrinogen (aa 36-52) peptides was determined with ELISA. The E2 antibody (also derived from a RA synovial B cell) reacts against human tetanus and was detected using ELISA (MyBioSource). Murinization of the human monoclonal antibodies was performed by replacing the full human IgG1 Fc by the murine IgG2a Fc.

Injection of Antibodies, CXCL1/CXCL2 and CXCR1/2 Antagonist

Mice were injected intravenously (i.v.) day 0 with either saline or human IgG (hACPA and controls 0.125-4 mg, human mAb ACPA (2 mg C03, B02 and B09 and control mAb G09, or B02 and B09 1:1) or murinzed mAb ACPA (2 mg, single Ab or D10 and B2 1:1 or B9 and B2 1:1) diluted in 100 µl saline.

Intra-articular injection was performed under isoflurane anesthesia. A mix of 15 ng CXCL1 (Sigma) and 15 ng CXCL2 (Sigma) was diluted in 3 µl saline and injected into the left ankle (tibio-tarsal) joint. The CXCR2 antagonist reparixin (L-lysin salt, HY-15252, MedChem Tronica) was injected subcutaneously (s.c. in 100 µl saline) twice daily (30 mg/kg/day).

Mechanical Hypersensitivity

Withdrawal thresholds of the hind paws were assessed using von Frey filaments as previously described (Bas, D. B. et al., 2012). In brief, the mice were habituated in individual compartments on top of a wire-mesh surface (Ugo Basile) prior to experiment. On test days, mice were given time to acclimatize and then optiHair filaments (Marstock OptiHair) of increasing buckling force (0.5, 1, 2, 4, 8, 16, and 32 mN) were applied to the plantar surface of the paw until the filament bent slightly. A brisk withdrawal of the paw within 2-3 seconds was noted as a positive response. A 50% withdrawal threshold was calculated using the Dixon up-down method (Chaplan, S. R., et al., 1994) and results from both hind paws were averaged and presented as % of baseline values.

After unilateral intra-articular injections only the result from the ipsilateral paw was used. In addition to presenting the results as 50% withdrawal threshold, data (FIG. 4E) were also presented as a hyperalgesic index, a calculation that defines the effect of reparixin treatment. It represents the area (based on withdrawal threshold in percent and time in days) between the extrapolated line from start of treatment (day 6) and the time-response curve after reparixin or saline injection. Increasing values indicate decreasing hypersensitivity. Mice were allocated to have even baseline tactile thresholds across groups and tests were performed between 10:00-15:00. Investigators blinded to treatments performed all behavior tests.

Thermal Sensitivity

Heat sensitivity was examined using a modified Hargreaves box (Dirig, D. M. et al., 1997). Mice were placed individually in Plexiglas cubicles on the glass surface and allowed to habituate. A radiant heat stimulus was then applied from below to a hind paw until a motion sensor detects a brisk withdrawal and stops the stimulus. Elapsed time is automatically recorded with a cutoff at 20 seconds. Three measurements from each paw were averaged and presented as latency (in seconds) for the withdrawal.

To assess sensitivity to cold, the mice were placed in the same testing device as used for detection of mechanical hypersensitivity. After habituation, a 1 ml syringe was used to gently apply a drop of acetone to the plantar surface of the hind paw and the duration of the nocifensive behavior (lifting, shaking, biting, and licking the paw) was recorded. The test was repeated three times on each paw and the average was calculated.

Locomotor Activity and Food/Water Consumption

Food and water consumption, and activity level of the mice during a full night cycle was measured using Oxymax/Comprehensive Lab Monitoring System (CLAMS, Columbus Instruments). Mice were habituated for 24 h in single housed testing cages before moved into the CLAMS just before the start of the night cycle (18:00-06:00 hours). Infrared sensors detected movement in X, Y and Z-axes and recorded the amount of beam breaks during the testing period. These values were then accumulated to show total movement over the whole 12 h night cycle. A feeder system connected to a scale and automated water device recorded consumption during the period. The data was presented as total movement (total number of XY-axis beam breaks), ambulation (number of consecutive XY-axis beam breaks), rearing (number of beam breaks in the Z-axis), food intake (g), and water intake (ml).

Metalloprotease Activity

Mice injected with either saline, 1 mg hACPA, or 4 mg anti-CII IgG (Nandakumar, K. S., et al., 2003) received i.v. injection of MMPsense 680 (2 nmoles in 150 µl PBS/mouse, PerkinElmer) 24 h before sacrifice. Paws were removed and scanned in an Odyssey CLx (LI-COR) near-infrared system. The signal intensity was quantified and normalized to saline injected mice and the data presented as a heat map.

Tissue Analysis

Mice were anesthetized using 4% isoflurane and blood withdrawn by cardiac puncture, followed by saline (with 2 U/ml heparin) perfusion to remove blood before different tissues were dissected, snap frozen and stored in −80° C. until further analyses.

Western Blot

The presence of human IgG antibodies (ACPA, FT, and IgG from healthy controls) in mouse tissues and plasma was assessed by Western blotting. Joints (ankle), dorsal root ganglia, adipose tissue (subcutaneous white), skin (plantar hind paw), spleen, lung, skeletal muscle (quadriceps), heart, kidney, liver, spinal cord (L4-L6), brain and bone marrow (tibial) were homogenized with protein extraction buffer (0.5% Triton X-100, 50 mM Tris, 150 mM NaCl, 1 mM EDTA and 1% SDS, pH 7.4) supplemented with proteases inhibitors (GE Healthcare). Supernatants from the homogenates as well as sera were mixed with LDS sample buffer (Invitrogen) containing DTT, and denatured at 70° C. for 10 minutes. Total proteins from the tissues homogenates and plasma (30 pg per well) were loaded onto NuPAGE® Bis-Tris 4-12% gels (Invitrogen) and run in MES-SDS antioxidant-containing running buffer at 200 V for 50 min. Proteins were transferred to a nitrocellulose membrane (Bio-Rad Laboratories) at 30V and blocked with 5% non-fat dry milk prepared in TBS containing 0.1% Tween 20 for 1 hour at room temperature. For the immunoblotting, membranes were incubated with the secondary antibody rabbit anti-human IgG HRP (1:10 000, sc-2769, Santa Cruz Biotechnology) for 1 hour at room temperature. The membranes were developed using the SuperSignal® West Pico chemiluminescent substrate (Thermo Scientific), according to manufacturer's instructions.

Joint Histology

Hind ankle joints and tibia from mice injected i.v. with saline, 1 mg hACPA, or arthritis induced with CAIA29 were post-fixed in 4% PFA for 48 h, decalcified in EDTA (Sigma) for 4-5 weeks, then dehydrated in ethanol and embedded in paraffin. Sections (5 µm) were cut and stained with hematoxylin and eosin (H&E, Histolab) and scored by blinded investigators on a scale from 0-3, where 0 represents normal and 3 represents severe synovitis, bone erosion, and/or cartilage destruction, as previously described (Bas, D. B. et al., 2012).

Bone structure (bone erosion) was analyzed using a SkyScan 1176 micro-CT (Bruker) with a voxel size of 9 µm. The method is disclosed in further detail in Krishnamurthy et al., 2016.

Quantitative Real-Time Polymerase Chain Reaction (PCR)

Ankle joints and plantar paw skin of the hind legs were processed for gene expression analysis. Muscle and tendons were removed from ankle joints, which were then snap frozen and pulverized. Tissues were sonicated in TRIzol (Invitrogen) and RNA was extracted according to manufacturer's protocol. After complementary DNA (cDNA) synthesis, quantitative real-time PCR (Applied Biosystems) was performed using hydrolysis probes to determine the relative messenger RNA (mRNA) levels. Primers for chemokines Ccl2 (MCP1, Mm00441242_m1), Cxcl1 (Mm04207460_m1), Cxcl2 (Mm00436450_m1), Cxcl5 (Mm00436451_g1), inflammatory cytokines Tnf (Mm00443258_m1), Il1b (Mm00434228_m1), Il6 (Mm00446190_m1), mast cell proteases Mcpt4 (Mcp4, Mm00487636-g1), Tpsb2 (Mcp6, Mm01301240-g1), pro-inflammatory enzyme Cox2 (Mm00478374_m1), matrix metallo proteases Mmp2 (Mm00439498_m1), Mmp9 (Mm00442991_m1), Mmp13 (Mm00439491-m1), and reference gene Hprt1 (Mm01545399_m1) (all from Applied Biosystems) were used to determine threshold cycle values to calculate the number of cell equivalents in each sample with the standard curve method. Data was normalized to Hprt1 values and expressed as relative expression units (REU).

Osteoclast Cultures

For in vitro osteoclasts generation, bone marrow cells were obtained from wildtype Balb/c mice (Harlan) and CD-11b+ cells were isolated using anti-CD-11b microbeads (Miltenyi Biotec Norden). CD-11b+ cells were seeded in 280×105 cells per well in DMEM containing 10% heat inactivated fetal bovine serum (FBS), 2 mM L-glutamine, 100 IU/ml penicillin and 50 µg/ml streptomycin (Sigma-Aldrich) and stimulated with M-CSF (Peprotech) 25 ng/ml and RANKL (Peprotech) 25 ng/ml. From day 6, either saline, ACPA, or FT was added to the media (1 µg/ml) purified from peripheral blood of RA patients and medium was replenished every two days with fresh supplements.

Osteoclasts were analyzed using Tartrate-resistant acid phosphatase (TRAP) staining by leukocyte acid phosphatase kit 387A (Sigma-Aldrich) following manufacture instructions. TRAP positive cells with not less than 3 nuclei were counted manually as osteoclasts in the Nikon inverted light microscope.

Chemokine Analysis

Level of CXCL1 (KC-GRO) and CXCL2 (MIP-2a) was measured in the supernatants from cultured CD-11b+ cells. Samples were analyzed using V-Plex immunoassay kit (Meso Scale Discovery, cat K152QTD-1) for CXCL1 and ELISA kit (R&D systems, cat MM200) for CXCL2, diluted 1:2 in assay diluents and according to the manufacturer's protocol. Limit of quantification (LOQ) was 0.8 pg/ml for CXCL1 and 7.8 pg/ml for CXCL2.

DRG Cell Culture.

DRGs (L6-C1) from Balb/c mice were extracted and placed in ice-cold Dulbecco's PBS until enzymatically dissociated with papain (1.7 mg/ml) (30 min at 37° C.) followed by a collagenase I (2 mg/ml) and dispase II (8 mg/ml) (Sigma) enzyme mix (30 min at 37° C.). The cells were then gently triturated in Leibovitz's medium supplemented with 10% heat-inactivated bovine serum, 1% penicillin and streptomycin (Invitrogen) and 10 µM mitotic inhibitor (5-fluoro-2-deoxyuridine, Sigma). The cell suspension was plated on uncoated well plates for 1.5-2 h before transferred to poly-D-lysine and laminin (Sigma) pre-coated well plates. The cells were maintained at 37° C. in 5% CO2 atmosphere and the medium replaced after 24 h and then every third day.

Statistical Analysis

For comparing changes in behavior and chemokine levels over time, repeated measures two-way analysis of variance (ANOVA) was used followed by Bonferroni post-hoc test. For differences in fluorescence, tactile thresholds, thermal thresholds, food/water consumption, body weight, and locomotion with three groups or more, one-way ANOVA was used, followed by Bonferroni post-hoc test.

For differences in mRNA levels, tactile thresholds and locomotion with two groups, Students t-test was used. Arthritis and histological scores were compared using the Kruskal-Wallis test followed by Dunn's multiple comparison post hoc test. All tests were performed using GraphPad Prism 6 software. P values less than 0.05 were considered significant. No statistical method was used to predetermine sample size.

Results

In conclusion, these observations demonstrate for the first time that RA-associated ACPA autoantibodies are able to induce pain-like behavior in mice, in the absence of visual, histological and biochemical signs of inflammation. Further, the data suggests that this effect is mediated via osteoclast activation and release of CXCL1, which activate nociceptive nerves that are abundantly present in joints and bone.

The present findings suggest that the arthralgia that often precedes the onset of RA or remains after inflammation and disease activity has diminished, may indeed be a direct consequence of the presence of certain ACPAs rather than being an unspecific symptom related to the pathogenesis of RA. This insight should dramatically alter the current approach to diagnosing as well as treating ACPA-positive arthralgia, and may indicate new potential targets for prevention of development of clinical signs of RA in this early phase of disease development. Such targets would obviously include both IL-8 and associated receptors and molecules in osteoclasts that contribute to the ACPA-induced production of IL-8. The studies show that similar mechanisms may be responsible for pain that remains also after joint inflammation has diminished in established arthritis, but where pain remains (remaining pain)

The findings also indicate that similar mechanisms, involving IL-8 produced from osteoclasts, with or without stimulation with ACPAs or other autoantibodies, may be responsible for induction of pain in many other conditions than RA, including for example osteoarthritis, but not limited thereto.

While IL-8 is a well-established inducer of non-stimulated osteoclast activation and bone destruction it is now shown for the first time that antibody-mediated bone destruction is IL-8 dependent both in vitro and now in vivo according to new data in mice where bone destruction induced by injected ACPA was completely reversed by reparixin.

The results clearly show that blockade of IL-8 receptors with specific receptor blockade (reparixin) blocks the activation of osteoclasts, and thus that blockade of the actions of IL-8 profoundly alters the behavior of osteoclasts, both concerning the release of IL-8 and its effects concerning bone destruction and osteopenia, and concerning the effects of IL-8 on pain. This enables new approaches to prevent or alleviate osteopenia and bone destruction with the inhibition or blockade of the action of IL-8. This is likely to be applicable in many conditions and diseases involving bone loss, but in particular in diseases where osteoclasts are stimulated with autoantibodies such as ACPAs. The results also show the potential to inhibit or alleviate pain using IL-8 inhibition or blockade in different conditions and diseases involving the contribution of IL-8 and osteoclasts, for example elevated IL-8 expression and/or the activation of osteoclasts.

The present findings may however also have other and broader implications: Firstly, they may provide a possible explanation to the remaining pain in some ACPA-positive RA patients who have been successfully treated for their inflammation; levels of ACPA do normally persist also after successful treatment of inflammation (Rönnelid, J. et al., 2005; Bos, W. H. et al., 2008).

Second, advancing the understanding of how autoantibodies, in addition to a role in inflammatory processes, contribute to long-term pain may aid in the identification of targets for pain control, also in other painful autoimmune diseases.

Thirdly, the currently demonstrated central role of IL-8 released from osteoclasts in generating pain affecting locomotion may be relevant also for additional diseases than RA that are associated with joint pain and/or "bone pain". One example is osteoarthritis, OA, in which the patients experience joint pain. IL-8 levels reaching 2000 pg/ml in the synovial fluid have been reported. Interesting tentative diseases that are thought to benefit from the disclosed methods of treatment, alleviation or prevention of pain and/or bone loss are virus-induced arthralgias such as Chikungunya fever, as well as cases of other alphavirus-induced arthralgia, which are interestingly associated with high serum levels of IL-8 and ostoclastogenesis (Hoarau, J.-J. et al., 2010; Phuklia, W. et al., 2013). In patients with Chikungunya fever, serum levels of IL-8 around 600 pg/ml have been reported (Reddy et al., 2014).

Effects of Monoclonal ACPA In Vivo

During the priority year, the inventors investigated the effect of different monoclonal anti-citrullinated protein antibodies (ACPA) in vivo, in the same animal model as disclosed previously in this specification, under "Methods". Monoclonal ACPAs were generated as disclosed, and the resulting pain was evaluated using the "Mechanical hypersensitivity" model disclosed herein.

It was found that monoclonal ACPAs C03, B09 and a mix of B02/609 (1:1) induced pain-like behavior. Control antibodies and B02 did not have this effect. Only the B02/B09 mix induced detectable bone erosion investigated using joint histology as described herein, in the "Methods" section.

Effect of Reparixin on Monoclonal ACPA C03 Induced Pain

In addition to the tests using reparixin accounted for earlier in this description, the inventors tested the effect of reparixin specifically on pain induced by the human monoclonal ACPA antibody C03. Reparixin was administered at a dose of 30 mg/kg, once a day, starting day 1, during the study. The results are shown in FIG. 8.

As a comparison, the tests were repeated using the peptidylarginine deiminase (PAD) enzyme inhibitors CI-amidine and 2-chloroacetamidine (2CA) in the same animal model, and the effect on pain induced by the human monoclonal ACPA antibody C03 investigated. CI-amidine was administered by subcutaneous injection at a dose of 10 mg/kg BW per day for a duration of 14 days. 2CA was also administered by subcutaneous injection, at a dose of 5 mg/kg BW per day for a duration of 14 days.

Comparative Examples Using Conventional Pain Relieving Drugs

In a series of comparative experiments, the effect of three conventional painkillers was tested. For naproxen and gabapentin, animals were injected with either the monoclonal human G09 ACPA antibody (hG09) or the monoclonal human ACPA antibody (hC03) and the effect of the painkillers investigated. As comparison, hG09 and saline was used. The animals were observed for 6 hours and the withdrawal thresholds tested at baseline, 1.5, 3 and 6 hours, according to the "mechanical hypersensitivity" model presented herein. As can be seen in FIG. 10, graphs A and B, naproxen and gabapentin had no detectable effect on pain, measured as withdrawal threshold.

Diclofenac was tested in a different set-up where the animals were injected with the human monoclonal antibodies hC03 and hB09G09, and observed during 6 hours. Diclofenac was administered at a dose of 30 mg/kg during days 7—7 when the mice exhibited ACPA induced pain. The results are shown in FIG. 10, graphs C and D.

The results obtained in the comparative examples strongly indicate the importance and advantages of the herein disclosed possibilities to treat pain associated with the contribution of IL-8 and osteoclasts.

Effect of an Osteoclast Inhibitor on ACPA C03 Induced Pain

Figure 11:
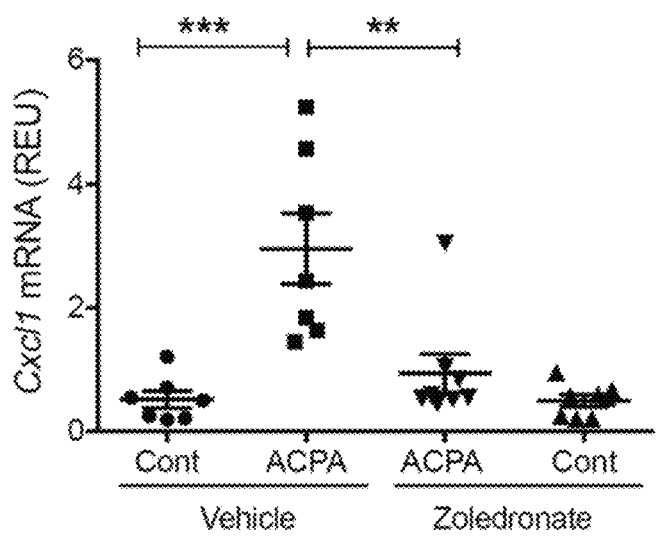

The inventors also investigated the effect of zoledronate (a bisphosphonate osteoclast inhibitor) on ACPA-induced pain behavior in the same animal models. Zoledronate was administered at the doses 10, 30 and 100 mg/kg BW for a duration of 10 days. The results are shown in FIG. 11.

A dose dependent effect was seen, and the effective dose range was found to be similar to that reported for prevention of ovariectomy-induced bone loss. See e.g. Green and Rogers, Pharmacologic profile of zoledronic acid: A highly potent inhibitor of bone resorption, in Drug Development Research, Volume 55, Issue 4, pages 210-224, April 2002.

Without further elaboration, it is believed that a person skilled in the art can, using the present description, including the examples, utilize the present invention to its fullest extent. Also, although the invention has been described herein with regard to its preferred embodiments, which constitute the best mode presently known to the inventors, it should be understood that various changes and modifications as would be obvious to one having the ordinary skill in this art may be made without departing from the scope of the invention which is set forth in the claims appended hereto.

Thus, while various aspects and embodiments have been disclosed herein, other aspects and embodiments will be apparent to those skilled in the art. The various aspects and embodiments disclosed herein are for purposes of illustra-

REFERENCES

Amara, K. et al. Monoclonal IgG antibodies generated from joint-derived B cells of RA patients have a strong bias toward citrullinated autoantigen recognition. J Exp Med 210, 445-455 (2013).

Arnett, F. C. et al. The American Rheumatism Association 1987 revised criteria for the classification of rheumatoid arthritis. Arthritis Rheum 31, 315-324 (1988).

Bas, D. B. et al. Collagen antibody-induced arthritis evokes persistent pain with spinal glial involvement and transient prostaglandin dependency. Arthritis Rheum 64, 3886-3896 (2012).

Bos, W. H. et al. Differential response of the rheumatoid factor and anticitrullinated protein antibodies during adalimumab treatment in patients with rheumatoid arthritis. The Journal of rheumatology 35, 1972-1977 (2008).

Bos, W. H. et al. Arthritis development in patients with arthralgia is strongly associated with anti-citrullinated protein antibody status: a prospective cohort study. Ann Rheum Dis 69, 490-494 (2010).

Cao, D.-L., Zhang, Z.-J., Xie, R.-G., Jiang, B.-C., Ji, R.-R., & Gao, Y.-J., Chemokine CXCL1 enhances inflammatory pain and increases NMDA receptor activity and COX-2 expression in spinal cord neurons via activation of CXCR2. Experimental Neurology, 2014 November; 261: 328-36.

Catrina A I, Joshua V, Klareskog L, Malmström V. Mechanisms involved in triggering rheumatoid arthritis, Immunol Rev. 2016 January; 269(1):162-74

Chaplan, S. R., Bach, F. W., Pogrel, J. W., Chung, J. M. & Yaksh, T. L. Quantitative assessment of tactile allodynia in the rat paw. Journal of neuroscience methods 53, 55-63 (1994).

Cobos, E. J. et al. Inflammation-induced decrease in voluntary wheel running in mice: a nonreflexive test for evaluating inflammatory pain and analgesia. Pain 153, 876-884 (2012).

Cui, G.-B., An, J.-Z., Zhang, N., Zhao, M.-G., Liu, S.-B., & Yi, J., Elevated interleukin-8 enhances prefrontal synaptic transmission in mice with persistent inflammatory pain. Molecular Pain, 2012 Feb. 12; 8(1), 11.

Cunha, T. M. et al. A cascade of cytokines mediates mechanical inflammatory hypernociception in mice. Proc Natl Acad Sci USA 102, 1755-1760 (2005).

Dirig, D. M., Salami, A., Rathbun, M. L., Ozaki, G. T. & Yaksh, T. L. Characterization of variables defining hindpaw withdrawal latency evoked by radiant thermal stimuli. Journal of neuroscience methods 76, 183-191 (1997). Nandakumar, K. S., Svensson, L. & Holmdahl, R. Collagen type II-specific monoclonal antibody-induced arthritis in mice: description of the disease and the influence of age, sex, and genes. Am. J. Pathol. 163, 1827-1837 (2003).

Endo et al., Experimental arthritis induced by continuous infusion of IL-8 into rabbit knee joints, Clinical and experimental Immunology, Vol. 96, Issue 1, 1 Apr. 1994

Green, Jonathan R. and Rogers, Michael J., Pharmacologic profile of zoledronic acid: A highly potent inhibitor of bone resorption, in Drug Development Research, Volume 55, Issue 4, pages 210-224, April 2002

Guerrero, A. T. G. et al. Toll-like receptor 2/MyD88 signaling mediates zymosan-induced joint hypernociception in mice: participation of TNF-α, IL-1β and CXCL1/KC. Eur J Pharmacol 674, 51-57 (2012).

Güler-Yüksel, M. et al. Changes in hand and generalised bone mineral density in patients with recent-onset rheumatoid arthritis. Ann Rheum Dis 68, 330-336 (2009).

Harre, U. et al. Induction of osteoclastogenesis and bone loss by human autoantibodies against citrullinated vimentin. J Clin Invest 122, 1791-1802 (2012).

Hoarau, J.-J. et al. Persistent chronic inflammation and infection by Chikungunya arthritogenic alphavirus in spite of a robust host immune response. J Immunol 184, 5914-5927 (2010).

Ibarra, J. M., Jimenez, F., Martinez, H. G., Clark, K. & Ahuja, S. S. MMP-Activated Fluorescence Imaging Detects Early Joint Inflammation in Collagen-Antibody-Induced Arthritis in CC-Chemokine Receptor-2-Null Mice, In-Vivo. Int J Inflam 2011, 691587 (2011).

Kim, S.-J., Park, S.-M., Cho, Y.-W., Jung, Y.-J., Lee, D.-G., Jang, S.-H., et al. (2011). Changes in expression of mRNA for interleukin-8 and effects of interleukin-8 receptor inhibitor in the spinal dorsal horn in a rat model of lumbar disc herniation. Spine, 36(25), 2139-2146.

Klein, C. J., Lennon, V. A., Aston, P. A., McKeon, A. & Pittock, S. J. Chronic pain as a manifestation of potassium channel-complex autoimmunity. Neurology 79, 1136-1144 (2012).

Kopesky, P. et al. Autocrine signaling is a key regulatory element during osteoclastogenesis. Biol Open 3, 767-776 (2014).

Krishnamurthy, A. et al. Identification of a novel chemokine-dependent molecular mechanism underlying rheumatoid arthritis-associated autoantibody-mediated bone destruction. Ann Rheum Dis. 2016 April; 75(4):721-9. (Epub 2015 Nov. 26)

Lee, Y. C. et al. Pain persists in DAS28 rheumatoid arthritis remission but not in ACR/EULAR remission: a longitudinal observational study. Arthritis Res Ther 13, R83 (2011).

Makrygiannakis, D., et al. Citrullination is an inflammation-dependent process. Ann Rheum Dis 65, 1219-1222 (2006)

Ossipova, E. et al. Affinity purified anti-citrullinated protein/peptide antibodies target antigens expressed in the rheumatoid joint. Arthritis Res Ther 16, R167 (2014).

Phuklia, W. et al. Osteoclastogenesis induced by CHIKV-infected fibroblast-like synoviocytes: a possible interplay between synoviocytes and monocytes/macrophages in CHIKV-induced arthralgia/arthritis. Virus Res. 177, 179-188 (2013).

Qin, X., Wan, Y. & Wang, X. CCL2 and CXCL1 trigger calcitonin gene-related peptide release by exciting primary nociceptive neurons. J. Neurosci. Res. 82, 51-62 (2005).

Rantapaa-Dahlqvist S, de Jong B A, Berglin E, Hallmans G, Wadell G, Stenlund H, Sundin U, van Venrooij W J, Antibodies against cyclic citrullinated peptide and IgA rheumatoid factor predict the development of rheumatoid arthritis, Arthritis Rheum. 2003 October; 48(10):2741-9.

Reddy V, Mani R S, Desai A, Ravi V, Correlation of plasma viral loads and presence of Chikungunya IgM antibodies with cytokine/chemokine levels during acute Chikungunya virus infection, J Med Virol. 2014 August; 86(8): 1393-401.

S. Riegsecker and S. Ahmed, FASEB, 2013; 27:643.18, 1 Apr. 2013

Russo, R. C., Garcia, C. C., Teixeira, M. M. & Amaral, F. A. The CXCL8/IL-8 chemokine family and its receptors in inflammatory diseases. Expert Rev Clin Immunol 10, 593-619 (2014).

Rönnelid, J. et al. Longitudinal analysis of citrullinated protein/peptide antibodies (anti-CP) during 5 year follow up in early rheumatoid arthritis: anti-CP status predicts worse disease activity and greater radiological progression. Ann Rheum Dis 64, 1744-1749 (2005).

Schellekens, G. A., de Jong, B. A., van den Hoogen, F. H., van de Putte, L. B. & van Venrooij, W. J. Citrulline is an essential constituent of antigenic determinants recognized by rheumatoid arthritis-specific autoantibodies. J Clin Invest 101, 273-281 (1998).

Tanaka et al., Modern Rheumatology, Vol. 22, issue 1, 1 Feb. 2012

Verri, W. A. et al. Hypernociceptive role of cytokines and chemokines: targets for analgesic drug development? Pharmacol. Ther. 112, 116-138 (2006).

Wang, J.-G. et al. The chemokine CXCL1/growth related oncogene increases sodium currents and neuronal excitability in small diameter sensory neurons. Molecular pain 4, 38 (2008).

White J R, Lee J M, Young P R, Hertzberg R P, Jurewicz A J, Chaikin M A, Widdowson K, Foley J J, Martin L D, Griswold D E, Sarau H M., Identification of a potent, selective non-peptide CXCR2 antagonist that inhibits interleukin-8-induced neutrophil migration, J Biol Chem. 1998 April 24; 273(17):10095-8.

Zhang, Z.-J., Cao, D.-L., Zhang, X., Ji, R.-R. & Gao, Y.-J. Chemokine contribution to neuropathic pain: respective induction of CXCL1 and CXCR2 in spinal cord astrocytes and neurons. Pain 154, 2185-2197 (2013).

The invention claimed is:

1. A method of alleviating joint pain without concurrent synovitis in a subject in need thereof, said method comprising administering to the subject an effective amount of a compound capable of inhibiting or blocking the action of IL-8,
wherein said joint pain without concurrent synovitis is associated with a presence of IL-8 and osteoclasts in the subject,
and
wherein said compound is selected from the group consisting of
reparixin (repertaxin, (2R)-2-[4-(2-methylpropyl)phenyl]-N-methylsulfonylpropanamide);
DF 2162 (4-[(1R)-2-amino-1-methyl-2-oxoetthyl]phenyl trifluoromethane sulfonate);
AZD8309 (5-[[(2,3-difluorophenyl)methyl]thio]-7 [[(1R)-2-hydroxy-1-methylethyl]amino]-thiazolo[4,5-d]pyrimidin-2(3H-one);
AZD5069 (N-[2-[[2,3-difluorophenyl)methyl]thio]-6-{[(1r,2s)-2,3-dihydroxy-1-methylpropyl]oxy}-4-pyrimidinyl]-1-azetidinesulfonamide);
PD0220245 (N-(3-[2,2'-bithiophen-5-yl]-6,7-dichloro-2-quinoxalinyl)-N,N-diethyl-butane-1,4-diamine dihydrochloride);
SB-332235 (1-(4-chloro-2-hydroxy-3-sulfamoylphenyl)-3-(2,3-dichlorophenyl)urea);
SCH-527123 (navarixin, 2-hydroxy-N,N-dimethyl-3-[[2-[[(1R)-1-(5-methylfuran-2-yl)propyl]amino]-3,4-dioxocyclobuten-1-yl]amino]benzamide);
SB-656933 (elubrixin, 1-(2-chloro-3-fluorophenyl)-3-(4-chloro-2-hydroxy-3-piperazin-1-ylsulfonylphenyl)urea);
SB-225002 (N-(2-bromophenyl)-N'-(2-hydroxy-4-nitrophenyl)urea); and
GSK1325756 (danirixin, 1-[4-chloro-2-hydroxy-3-[(3S)-piperidin-3-yl]sulfonylphenyl]-3-(3-fluoro-2-methylphenyl)urea).

2. The method according to claim 1, wherein said compound is reparixin (repertaxin, (2R)-2-[4-(2-methylpropyl) phenyl]-N-methylsulfonylpropanamide).

3. The method according to claim 1, wherein said compound is danirixin (1-[4-chloro-2-hydroxy-3-[(3S)-piperidin-3-yl]sulfonylphenyl]-3-(3-fluoro-2-methylphenyl)urea.

4. A method of alleviating joint pain without concurrent synovitis in a subject in need thereof, said method comprising administering to the subject an effective amount of a compound capable of inhibiting or blocking the action of IL-8,
wherein said joint pain without concurrent synovitis is associated with a presence of IL-8 and osteoclasts in the subject,
wherein IL-8 activation of the osteoclasts is associated with a presence of autoantibodies in said subject,
and
wherein said compound is selected from the group consisting of
reparixin (repertaxin, (2R)-2-[4-(2-methylpropyl)phenyl]-N-methylsulfonylpropanamide);
DF 2162 (4-[(1R)-2-amino-1-methyl-2-oxoetthyl]phenyl trifluoromethane sulfonate);
AZD8309 (5-[[(2,3-difluorophenyl)methyl]thio]-7 [[(1R)-2-hydroxy-1-methylethyl]amino]-thiazolo[4,5-d]pyrimidin-2(3H-one);
AZD5069 (N-[2-[[2,3-difluorophenyl)methyl]thio]-6-{[(1r,2s)-2,3-dihydroxy-1-methylpropyl]oxy}-4-pyrimidinyl]-1-azetidinesulfonamide);
PD0220245 (N-(3-[2,2'-bithiophen-5-yl]-6,7-dichloro-2-quinoxalinyl)-N,N-diethyl-butane-1,4-diamine dihydrochloride);
SB-332235 (1-(4-chloro-2-hydroxy-3-sulfamoylphenyl)-3-(2,3-dichlorophenyl)urea);
SCH-527123 (navarixin, 2-hydroxy-N,N-dimethyl-3-[[2-[[1 R)-1-(5-methylfuran-2-yl)propyl]amino]-3,4-dioxocyclobuten-1-yl]amino]benzamide);
SB-656933 (elubrixin, 1-(2-chloro-3-fluorophenyl)-3-(4-chloro-2-hydroxy-3-piperazin-1-ylsulfonylphenyl)urea);
SB-225002 (N-(2-bromophenyl)-N'-(2-hydroxy-4-nitrophenyl)urea); and
GSK1325756 (danirixin, 1-[4-chloro-2-hydroxy-3-[(3S)-piperidin-3-yl]sulfonylphenyl]-3-(3-fluoro-2-methylphenyl)urea).

5. The method according to claim 4, wherein said autoantibodies are anti-citrullinated protein antibodies (ACPA).

6. The method according to claim 4, wherein said compound is reparixin (repertaxin, (2R)-2-[4-(2-methylpropyl) phenyl]-N-methylsulfonylpropanamide).

7. The method according to claim 4, wherein said compound is danirixin, 1-[4-chloro-2-hydroxy-3-[(3S)-piperidin-3-yl]sulfonylphenyl]-3-(3-fluoro-2-methylphenyl)urea.

8. The method according to claim 4, wherein said autoantibodies are detectable in a sample taken from said subject, using an enzyme-linked immunosorbent assay (ELISA) for qualitative and semi-qualitative determination of IgG antibodies to Cyclic Citrullinated Peptides (CCP).

9. The method according to claim 8, wherein said subject is suffering from an autoimmune disease selected from rheumatoid arthritis, osteoarthritis, and arthralgia.

* * * * *